(12) United States Patent
Pancoska et al.

(10) Patent No.: US 7,846,669 B2
(45) Date of Patent: Dec. 7, 2010

(54) POLYNUCLEOTIDES FOR USE AS TAGS AND TAG COMPLEMENTS, MANUFACTURE AND USE THEREOF

(75) Inventors: Petr Pancoska, Mount Sinai, NY (US); Vit Janota, Praha (CZ); Albert S. Benight, Portland, OR (US); Richard S. Bullock, Chicago, IL (US); Peter V. Riccelli, Tinley Park, IL (US); Daniel Kobler, Ontario (CA); Daniel Fieldhouse, Bolton (CA)

(73) Assignee: Luminex Molecular Diagnostics, Inc., Toronto (CA)

( * ) Notice: Subject to any disclaimer, the term of this patent is extended or adjusted under 35 U.S.C. 154(b) by 0 days.

(21) Appl. No.: 12/576,902

(22) Filed: Oct. 9, 2009

(65) Prior Publication Data

US 2010/0216134 A1    Aug. 26, 2010

Related U.S. Application Data

(63) Continuation of application No. 11/729,302, filed on Mar. 28, 2007, now Pat. No. 7,608,398, which is a continuation of application No. 10/470,107, filed as application No. PCT/CA02/00087 on Jan. 25, 2002, now Pat. No. 7,226,737.

(60) Provisional application No. 60/263,710, filed on Jan. 25, 2001, provisional application No. 60/303,799, filed on Jul. 10, 2001.

(51) Int. Cl.
  *C12Q 1/68* (2006.01)
  *C07H 21/04* (2006.01)
  *C12N 15/11* (2006.01)

(52) U.S. Cl. .......................... 435/6; 536/23.1

(58) Field of Classification Search ................ None
See application file for complete search history.

(56) References Cited

U.S. PATENT DOCUMENTS

| | | |
|---|---|---|
| 4,851,331 A | 7/1989 | Vary et al. |
| 4,942,124 A | 7/1990 | Church |
| 5,002,867 A | 3/1991 | Macevicz |
| 5,149,625 A | 9/1992 | Church et al. |
| 5,391,480 A | 2/1995 | Davis et al. |
| 5,604,097 A | 2/1997 | Brenner |
| 5,635,400 A | 6/1997 | Brenner et al. |
| 5,654,413 A | 8/1997 | Brenner et al. |
| 5,830,539 A | 11/1998 | Yan et al. |
| 5,846,719 A | 12/1998 | Brenner et al. |
| 5,863,722 A | 1/1999 | Brenner |
| 5,981,176 A | 11/1999 | Wallace |
| 6,013,445 A | 1/2000 | Albrecht et al. |
| 6,040,138 A | 3/2000 | Lockhart et al. |
| 6,103,463 A | 8/2000 | Chetverin et al. |
| 6,150,095 A | 11/2000 | Southern et al. |
| 6,150,516 A | 11/2000 | Brenner et al. |
| 6,205,444 B1 | 3/2001 | Floratos et al. |
| 6,287,778 B1 | 9/2001 | Huang et al. |
| 6,322,971 B1 | 11/2001 | Chetverin et al. |
| 6,458,530 B1 | 10/2002 | Morris et al. |
| 6,472,157 B1 | 10/2002 | Di Rienzo et al. |
| 7,157,564 B1 | 1/2007 | Mittmann et al. |
| 7,226,737 B2 | 6/2007 | Pancoska et al. |
| 7,608,398 B2 | 10/2009 | Pancoska et al. |
| 7,645,868 B2 | 1/2010 | Kobler et al. |
| 2002/0177141 A1 | 11/2002 | Chee et al. |
| 2005/0089851 A1 | 4/2005 | Pancoska et al. |
| 2005/0191625 A1 | 9/2005 | Kobler et al. |
| 2007/0244310 A1 | 10/2007 | Pancoska et al. |
| 2008/0014587 A1 | 1/2008 | Pancoska et al. |
| 2010/0112705 A1 | 5/2010 | Pancoska et al. |

FOREIGN PATENT DOCUMENTS

| | | |
|---|---|---|
| EP | 0698792 | 2/1996 |
| EP | 0799897 | 10/1997 |
| WO | WO-93/17126 | 9/1993 |
| WO | WO-97/31256 | 8/1997 |
| WO | WO-00/58516 | 10/2000 |
| WO | WO-01/59151 | 8/2001 |
| WO | WO-02/053728 | 7/2002 |
| WO | WO-02/059354 A3 | 8/2002 |
| WO | WO-02/059355 A3 | 8/2002 |

OTHER PUBLICATIONS

Niemeyer, et al., (1999) "DNA-directed immobilization: Efficient, reversible, and site-selective surface binding of proteins by means of covalent DNA-streptavidin conjugates," Analytical Biochemistry, 268(1):54-63.

Southern, et al., (1999) "Molecular Interactions on Microarrays," Nature Genetics, 21:5-9.

Breslauer, et al., (1986) "Predicting DNA duplex stability from the base sequence," Proc. Natl. Acad. Sci. USA, 83:3746-3750.

Caruthers, et al., (1987) "Chemical Synthesis of Deoxyoligonucleotides by the Phosphoramidite Method," Methods in Enzymology 54:287-313.

Church, et al., (1988) "Multiplex DNA Sequencing," Science, 240:185-188.

Kwoh. et al., (1989) "Transcription-based amplification system and detection of amplified human immunodeficiency virus type 1 with a bead-based sandwich hybridization format," Proc. Natl. Acad. Sci. USA, 86:1173-1177.

Rychlik, et al., (1989) "A computer program for choosing optimal oligonucleotides for filter hybridization, sequencing and in vitro amplification of DNA," Nucleic Acids Research, 17(21):8543-8551.

Fodor, et al., (1991) "Light-directed, Spatially Addressable Parallel Chemical Synthesis," Science, 251:767-773.

Needels, et al., (1993) "Generation and screening of an oligonucleotide-encoded synthetic peptide library," Proc. Natl. Acad. Sci. USA, 90:10700-10704.

(Continued)

*Primary Examiner*—James Martinell
(74) *Attorney, Agent, or Firm*—Goodwin Procter LLP

(57) ABSTRACT

A family of minimally cross-hybridizing nucleotide sequences, methods of use, etc. A specific family of 210 24mers is described.

28 Claims, 4 Drawing Sheets

OTHER PUBLICATIONS

Ausubel, et al., (1993) "Short Protocols in Molecular Biology," 15-16 through 15-21.

Alper J., (1994) "Drug Discovery on the Assembly Line," Science, 264:1399-1401.

Nikiforov, et al., (1994),"Genetic Bit Analysis: a solid phase method for typing single nucleotide polymorphisms," Nucleic Acids Research, 22(20):4167-4175.

Southern, et al., (1994) "Arrays of complementary oligonucleotide for analyzing the hybridisation behaviour of nucleic acids," Nucleic Acids Research, 22(8):1368-1373.

Hensel, et al., (1995) "Simultaneous Identification of Bacterial Virulence Genes by Negative Selection," Science, 269:400-403.

Lyttle, et al., (1995) "Mutagenesis Using Trinucleotide β-Cyanoethyl Phosphoramidites," Bio Techniques, 19(2):274-280.

Matson, et al., (1995) "Biopolymer Synthesis on Polypropylene Supports: Oligonucleotide Arrays," Analytical Biochemistry, 224:110-116.

Shoemaker, et al., (1996) "Quantitative phenotypic analysis of yeast deletion mutants using a highly parallel molecular bar-coding strategy," Nature Genetics,14:450-456.

Hermanson, et al., (1996) "Bioconjugate Techniques," Academic Press, pp. 640-671.

Head, et al., (1997) "Nested genetic bit analysis (N-GBA) for mutation detection in the p53 tumor suppressor gene," Nucleic Acids Research, 25(24):5065-5071.

Weiler, et al., (1997) "Hybridisation based DNA screening on peptide nucleic acid (PNA) oligomer arrays," Nucleic Acids Research, 25(14):2792-2799.

Proudnikov, et al., (1998) "Immobilization of DNA in Polyacrylamide Gel for the Manufacture of DNA and DNA-Oligonucleotide Microchips," Analytical Biochemistry, 259:34-41.

Robertson, et al., (1998) "An Introduction to PCR Primer Design and Optimization of Amplification Reactions", Methods in Molecular Biology, 98:121-154.

Peyret, et al., (1999) "Nearest-Neighbor Thermodynamics and NMR of DNA Sequences with Internal A•A, C•C, G•G, and T•T Mismatches," Biochemistry, 38:3468-3477.

Lipshutz, et al., (1999) "High density synthetic oligonucleotide arrays", Nature Genetics Supplement, 21:20-24.

Hacia, et al., (1999) "Design of modified oligodeoxyribonucleotide probes to detect telomere repeat sequences in FISH assays," Nucleic Acids Research, 27(20):4034-4039.

Nguyen, et al., (1999) "Smoothing of the thermal stability of DNA duplexes by using modified nucleosides and chaotropic agents," Nucleic Acids Research, 27(6):1492-1498.

Iannone, et al., (2000) "Multiplexed Single Nucleotide Polymorphism Genotyping by Oligonucleotide Ligation and Flow Cytometry", Cytometry, 39:131-140.

Kane, et al., (2000) "Assessment of the sensitivity and specificity of oligonucleotide (50mer) microarrays," Nucleic Acids Research, 28(22):4552-4557.

Zammatteo, et al., (2000) "Comparison between different strategies of covalent attachment of DNA to glass surfaces to build DNA microarrays,"Analytical Biochemistry, 280:143-150.

Brenner, et al., (1992) "Encoded combinatorial chemistry," Proc. Natl. Acad. Sci. USA, 89:5381-5383.

Brenner, et al., (2000) "In vitro cloning of complex mixtures of DNA on microbeads: Physical separation of differentially expressed cDNAs," PNAS,97:1665-1670.

Brenner, et al., (2000) "Gene expression analysis by massively parallel signature sequencing (MPSS) on microbead arrays," Nature Biotech.,18:630-634.

Chetverin, et al., (1994) "Oligonucleotide Arrays: New Concepts and Possibilities," Bio/Technology, 12:1093-1099.

Frutos, et al., (1997) "Demonstration of a word design strategy for DNA computing on surfaces," NAR, 25(23):4748-4757.

Matthews, et al., (1988) "Analytical Strategies for the Use of DNA Probes," Analytical Biochemistry, 169:1-25.

Morgan, et al., (1994) "Simple and Efficient cDNA Capture Utilising a Short Gene-Specific Probe attached to Magnetic Beads," Biochem. Soc. Trans., 22:453S.

Ohleymer, et al., (1993) "Complex Synthetic Chemical Libraries Indexed with Molecular Tags," PNAS, 90:10922-10926.

Sasaki, et al., (1994) "Construction of a Normalized cDNA Library by Introduction of a Semi-Solid mRNA-cDNA Hybridization System," NAR, 22:987-992.

Ben-Dor, et al., (2000) "Universal DNA Tag Systems: A Combinatorial Design Scheme," J. Comput. Biol.,7(3-4):503-519.

Kececioglu, et al., (1995) "Combinatorial algorithms for DNA sequence assembly," Algorithmica, 13:7-51 (enclosed as p. 1-45).

Michael, et al., (1998) "Randomly Ordered Addressable High-Density Optical Sensor Arrays," Analytical Chemistry, 70:1242-1248.

Definition of "stringency," at http://cancerweb.ncl.ac.uk. Dec. 16, 1997. Accessed online Jan. 21, 2008.

Byrd, et al. (2000) "The Limitations of MALDI-TOF Mass Spectrometry in the Analysis of Wide Polydisperse Polymers," Analytical Chemistry 72:4568-4576.

Maskos, et al., (1993) "A Study of Oligonucletoide Reassociation Using Large Arrays of Olionucleotides Synthesised on a Glass Support," Nucleic Acids Research, 21:4663-4669.

Southern, et al., (1994) "Parallel Synthesis and Analysis of Large Numbers of Related Chemical Compounds: Application to Oligonucleotides," Journal of Biotechnology, 35:217-227.

Menkoth, et al., (1984) "Hybridization of Nucleic Acids Immobilized on Solid Supports," Analytical Biochemistry, 138:267-284.

Sonina, et al., (1989) "Dialect-I Species-specific Repeated DNA Sequence from Barley, *Hordeum* Vulgare," Theor. Appl. Genet., 78:589-593.

```
                        SEQUENCE LISTING

<160> NUMBER OF SEQ ID NOS: 217

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 1
gatttgtatt gattgagatt aaag                                            24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 2
tgattgtagt atgtattgat aaag                                            24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 3
gattgtaaga tttgataaag tgta                                            24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 4
gatttgaaga ttattggtaa tgta                                            24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 5
gattgattat tgtgatttga attg                                            24

<210> SEQ ID NO 6
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 6
gatttgattg taaaagattg ttga                                              24

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 7
attggtaaat tggtaaatga attg                                              24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 8
attggatttg ataaaggtaa atga                                              24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 9
gtaagtaatg aatgtaaaag gatt                                              24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 10
gattgattga ttgattgatt tgat                                              24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 11
tgatgattaa agaaagtgat tgat                                              24

<210> SEQ ID NO 12
<211> LENGTH: 24
<212> TYPE: DNA
```

```
<213> ORGANISM: Artificial Sequence
<220> FEATURE:
<223> OTHER INFORMATION: Description of Artificial Sequence:Artificially
      Synthesized DNA Sequence

<400> SEQUENCE: 12
aaaggatttg attgataaag tgat                                          24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 13
tgtagatttg tatgtatgta tgat                                          24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 14
gatttgataa agaaaggatt gatt                                          24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 15
gattaaagtg attgatgatt tgta                                          24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 16
aaagaaagaa agaaagaaag tgta                                          24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 17
tgtaaaagga ttgatttgta tgta                                          24

<210> SEQ ID NO 18
<211> LENGTH: 24
<212> TYPE: DNA
<213> ORGANISM: Artificial Sequence
```

```
<220> FEATURE:
<223> OTHER INFORMATION: Description of Artificial Sequence:Artificially
      Synthesized DNA Sequence

<400> SEQUENCE: 18
aaagtgtaga ttgattaaag aaag                                              24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 19
aaagttgatt gattgaaaag gtat                                              24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 20
ttgattgaga ttgattttga gtat                                              24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 21
tgaattgatg aatgaatgaa gtat                                              24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 22
gtaatgaagt atgtatgtaa gtaa                                              24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 23
tgatgatttg aatgaagatt gatt                                              24

<210> SEQ ID NO 24
<211> LENGTH: 24
<212> TYPE: DNA
<213> ORGANISM: Artificial Sequence
<220> FEATURE:
```

<223> OTHER INFORMATION: Description of Artificial Sequence:Artificially
      Synthesized DNA Sequence

<400> SEQUENCE: 24
tgataaagtg ataaaggatt aaag                                              24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 25
tgatttgagt atttgagatt ttga                                              24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 26
tgtagtaaga ttgattaaag gtaa                                              24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 27
gtataaagga ttgattttga aaag                                              24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 28
gtatttgagt aagtaattga ttga                                              24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 29
gtaaaaagtt gagtattgaa aaag                                              24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence:Artificially

```
Synthesized DNA Sequence

<400> SEQUENCE: 30
gatttgataa aggatttgta ttga                                              24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 31
gattgtattg aagtattgta aaag                                              24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 32
tgatgatttt gatgaaaaag ttga                                              24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 33
tgatttgaga ttaaagaaag gatt                                              24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 34
tgattgaatt gagtaaaaag gatt                                              24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 35
aaagtgtaaa aggatttgat gtat                                              24

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 36
aaaggtattt gagatttgat tgaa                                              24

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 37
aaagttgaga tttgaatgat tgaa                                              24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 38
tgtattgaaa aggtatgatt tgaa                                              24

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 39
gtattgtatt gaaaaggtaa ttga                                              24

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 40
ttgagtaatg ataaagtgaa gatt                                              24

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 41
tgaagatttg aagtaattga aaag                                              24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

-continued

```
<400> SEQUENCE: 42
tgaaaaagtg tagatttga gtaa                                           24

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 43
tgtatgaatg aagatttgat tgta                                          24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 44
aaagttgagt attgatttga aaag                                          24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 45
gatttgtaga tttgtattga gatt                                          24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 46
aaagaaagga tttgtagtaa gatt                                          24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 47
gtaaaaagaa aggtataaag gtaa                                          24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 48
```
gattaaagtt gattgaaaag tgaa                                        24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 49 tgaaaaggt aattgatgta tgaa                                         24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 50
aaaggattaa agtgaagtaa ttga                                        24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 51
atgaattggt atgtatatga atga                                        24

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 52
tgaaatgaat gaatgatgaa attg                                        24

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 53
attgattgtg aatgaaatga attg                                        24

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 54
attgaaagat gaaagatga aaag						24

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 55
attgttgaaa agtgtaatga ttga						24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 56
atgatgtaat gaaaagattg tgta						24

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 57
aaagattgaa agatgatgta attg						24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 58
attgatgagt atattgtgta gtaa						24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 59
aaagattgtg taattgatga tgaa						24

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 60
aaaggtatat tgtgtaatga gtaa						24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 61
tgtaatgagt attgtaattg aaag                                      24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 62
gtataaagaa agattggtaa atga                                      24

<210> SEQ ID NO 63
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 63
ttgagtaatt gaattgtgaa atga                                      24

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 64
tgtattgaat gaattgttga tgta                                      24

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 65
tgtaattggt aaatgagtaa aaag                                      24

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 66
tgaatgaaat tgatgagtat aaag                                      24

```
<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 67
gtaagtaaat tgaaagattg atga                                              24

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 68
gtaaatgatg atattggtat attg                                              24

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 69
attgttgatg attgattgaa atga                                              24

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 70
attgtgaagt ataaagatga ttga                                              24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 71
atgaaaagtt gagtaaattg tgat                                              24

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 72
atgaattgaa agtgattgaa aaag                                              24
```

<210> SEQ ID NO 73
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 73
gtaaattgat gaaaagttga tgat          24

<210> SEQ ID NO 74
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 74
aaagtgatgt atatgagtaa attg          24

<210> SEQ ID NO 75
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 75
gtaatgataa agatgatgat attg          24

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 76
ttgaaaagat tggtaatgat atga          24

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 77
aaagtgaaaa agattgattg atga          24

<210> SEQ ID NO 78
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 78
attgatgaga ttgattattg tgta          24

<210> SEQ ID NO 79

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 79
atgagattat tggatttgta gatt                                              24

<210> SEQ ID NO 80
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 80
tgaagattat gaattggtaa gatt                                              24

<210> SEQ ID NO 81
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 81
attggattat gagattatga ttga                                              24

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 82
attgttgaat tggattaaag atga                                              24

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 83
aaagatgagt aagtaaattg gatt                                              24

<210> SEQ ID NO 84
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 84
aaaggtaaga ttattgatga aaag                                              24

<210> SEQ ID NO 85
<211> LENGTH: 24
```

-continued

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 85
attgatgaga ttaaagttga attg                                              24

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 86
gattattgga ttatgaaaag gatt                                              24

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 87
gatttgtaat tgttgagtaa atga                                              24

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 88
aaagaaagat tgttgagatt atga                                              24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 89
gtataaagga ttttgaattg atga                                              24

<210> SEQ ID NO 90
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 90
ttgagattgt aaatgaattg ttga                                              24

<210> SEQ ID NO 91
<211> LENGTH: 24
<212> TYPE: DNA
```

```
<213> ORGANISM: Artificial Sequence
<220> FEATURE:
<223> OTHER INFORMATION: Description of Artificial Sequence:Artificially
      Synthesized DNA Sequence

<400> SEQUENCE: 91
gtatattgat tgtgtaatga aaag                                          24

<210> SEQ ID NO 92
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 92
tgatatgaat tggattattg gtat                                          24

<210> SEQ ID NO 93
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 93
atgaatgatg aatgatgatt attg                                          24

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 94
atgaattgat tggattgtaa tgat                                          24

<210> SEQ ID NO 95
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 95
gattgtaatt gagtaaattg atga                                          24

<210> SEQ ID NO 96
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 96
gattattgga ttaaaggtaa atga                                          24

<210> SEQ ID NO 97
<211> LENGTH: 24
<212> TYPE: DNA
<213> ORGANISM: Artificial Sequence
```

```
<220> FEATURE:
<223> OTHER INFORMATION: Description of Artificial Sequence:Artificially
      Synthesized DNA Sequence

<400> SEQUENCE: 97
attgttgaat tgatgagatt tgat                                              24

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 98
gattatgagt aaattgattg tgat                                              24

<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 99
gattattgtt gatgaatgat attg                                              24

<210> SEQ ID NO 100
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 100
tgtaaaagat tgaaggtat gatt                                               24

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 101
gtatttagat gagtttgtta gatt                                              24

<210> SEQ ID NO 102
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 102
tgaagttatg taatagaaag tgat                                              24

<210> SEQ ID NO 103
<211> LENGTH: 24
<212> TYPE: DNA
<213> ORGANISM: Artificial Sequence
<220> FEATURE:
```

<223> OTHER INFORMATION: Description of Artificial Sequence:Artificially
Synthesized DNA Sequence

<400> SEQUENCE: 103
gtatgtattg tatgtagtta attg                                      24

<210> SEQ ID NO 104
<211> LENGTH: 24
<212> TYPE: DNA
<213> ORGANISM: Artificial Sequence
<220> FEATURE:
<223> OTHER INFORMATION: Description of Artificial Sequence:Artificially
Synthesized DNA Sequence

<400> SEQUENCE: 104
tgatatagat agttagatag atag                                      24

<210> SEQ ID NO 105
<211> LENGTH: 24
<212> TYPE: DNA
<213> ORGANISM: Artificial Sequence
<220> FEATURE:
<223> OTHER INFORMATION: Description of Artificial Sequence:Artificially
Synthesized DNA Sequence

<400> SEQUENCE: 105
atgatgatgt attgtagtta tgaa                                      24

<210> SEQ ID NO 106
<211> LENGTH: 24
<212> TYPE: DNA
<213> ORGANISM: Artificial Sequence
<220> FEATURE:
<223> OTHER INFORMATION: Description of Artificial Sequence:Artificially
Synthesized DNA Sequence

<400> SEQUENCE: 106
ttagtgaatg tattagttga tgta                                      24

<210> SEQ ID NO 107
<211> LENGTH: 24
<212> TYPE: DNA
<213> ORGANISM: Artificial Sequence
<220> FEATURE:
<223> OTHER INFORMATION: Description of Artificial Sequence:Artificially
Synthesized DNA Sequence

<400> SEQUENCE: 107
gttagttaga ttattgttag ttag                                      24

<210> SEQ ID NO 108
<211> LENGTH: 24
<212> TYPE: DNA
<213> ORGANISM: Artificial Sequence
<220> FEATURE:
<223> OTHER INFORMATION: Description of Artificial Sequence:Artificially
Synthesized DNA Sequence

<400> SEQUENCE: 108
gttaattgtg tagtttgtta ttga                                      24

<210> SEQ ID NO 109
<211> LENGTH: 24
<212> TYPE: DNA
<213> ORGANISM: Artificial Sequence
<220> FEATURE:
<223> OTHER INFORMATION: Description of Artificial Sequence:Artificially Synthesized DNA Sequence

<400> SEQUENCE: 109
gttatgaaat agtgatattg ttag                                    24

<210> SEQ ID NO 110
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 110
attgttagaa agtgtagatt aaag                                    24

<210> SEQ ID NO 111
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 111
atgagtatgt tattagtgta tgta                                    24

<210> SEQ ID NO 112
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 112
tgtaatagtg aagttagatt gtat                                    24

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 113
attgatagat gattagttag ttga                                    24

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 114
atgagtttgt ttatgagatt aaag                                    24

<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

```
<400> SEQUENCE: 115
tgatgtttga ttatgatgta gtat                                              24

<210> SEQ ID NO 116
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 116
atgagttagt tatgaattag atga                                              24

<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 117
attgttagtg atgttagtaa ttag                                              24

<210> SEQ ID NO 118
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 118
tgatgtaagt attgatgtta gttt                                              24

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 119
gattgtaaat agaaagtgaa gtaa                                              24

<210> SEQ ID NO 120
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 120
attgtgtatg aagtattgta tgat                                              24

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

```
<400> SEQUENCE: 121
atagtgatgt tatgaagatt gtta                                          24

<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 122
ttagatgaat tgtgaagtat ttag                                          24

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 123
gtaagttatg attgatgtta tgaa                                          24

<210> SEQ ID NO 124
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 124
gtattgatgt ttaaagtgta atag                                          24

<210> SEQ ID NO 125
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 125
gattgtaagt aagattgtat attg                                          24

<210> SEQ ID NO 126
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 126
gtttgtattt agatgaatag aaag                                          24

<210> SEQ ID NO 127
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 127
```
gtttgatttg taatagtgat tgta					24

<210> SEQ ID NO 128
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 128
tgtatgtagt atttagaaag atga					24

<210> SEQ ID NO 129
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 129
atgaattgtg ataagaaag ttag					24

<210> SEQ ID NO 130
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 130
ttagtgtagt aagtttaaag tgta					24

<210> SEQ ID NO 131
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 131
gtatgattgt ttgtaattag tgat					24

<210> SEQ ID NO 132
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 132
gtttaaagtt agttgagtta gtat					24

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 133
atagtgtatg tagattatga gatt                                           24

<210> SEQ ID NO 134
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 134
ttgaatgatt agttgagtat gatt                                           24

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 135
gtatgtaagt tagtatgatt tgaa                                           24

<210> SEQ ID NO 136
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 136
tgtagtatat tgttgaattg tgat                                           24

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 137
atagtgattg tatgtatgat aaag                                           24

<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 138
ttagtgattg atgtatattg aaag                                           24

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 139
gtaagattat gagttatgat gtaa                                           24

<210> SEQ ID NO 140
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 140
gttatgaaat tgttagtgta gatt                                          24

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 141
gttagatttg tagtttaaag atag                                          24

<210> SEQ ID NO 142
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 142
ttagtgattg aaatgatgta gatt                                          24

<210> SEQ ID NO 143
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 143
aaagtgtagt tattagttag ttag                                          24

<210> SEQ ID NO 144
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 144
aaagaaagtg tatgatgtta ttag                                          24

<210> SEQ ID NO 145
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 145
gattgtatat tgtgtatgat gatt                                          24

```
<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 146
ttgagattgt tatgatatga gtat                                          24

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 147
atgagtatga ttgttatgat gttt                                          24

<210> SEQ ID NO 148
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 148
tgatttagtg aaattgtgta ttag                                          24

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 149
tgaatgtatg tagtatgttt gtta                                          24

<210> SEQ ID NO 150
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 150
gttagtattg atgattatga gtta                                          24

<210> SEQ ID NO 151
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 151
gtatattgtg atttagttga gatt                                          24
```

```
<210> SEQ ID NO 152
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 152
gttagtttaa agttgagatt gttt                                           24

<210> SEQ ID NO 153
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 153
gtatattgtt agatgagatt tgta                                           24

<210> SEQ ID NO 154
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 154
tgatgtatgt tagtttatga atga                                           24

<210> SEQ ID NO 155
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 155
tgtagtatgt aatgtagtat ttga                                           24

<210> SEQ ID NO 156
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 156
atgagttatg tattgagtta gtat                                           24

<210> SEQ ID NO 157
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 157
tgtatgatga ttatagttga gtaa                                           24

<210> SEQ ID NO 158
```

```
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 158
attgatgaat gagtttgtat aaag                                              24

<210> SEQ ID NO 159
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 159
ttgagtttat gattagaaag aaag                                              24

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 160
tgatattgat gagttagtat tgaa                                              24

<210> SEQ ID NO 161
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 161
atagaaagtg aaatgagtat gtta                                              24

<210> SEQ ID NO 162
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 162
ttgatgtaga tttgatgtat atag                                              24

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 163
ttgagattat agtgtagttt atag                                              24

<210> SEQ ID NO 164
<211> LENGTH: 24
```

```
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 164
tgatgttaga ttgtttgatt attg                                              24

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 165
tgtattagat agtgatttga atga                                              24

<210> SEQ ID NO 166
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 166
gattatgatg aatgtagtat gtaa                                              24

<210> SEQ ID NO 167
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 167
tgaatgattg atatgaatag tgta                                              24

<210> SEQ ID NO 168
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 168
gtaatgattt agtgtattga gttt                                              24

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 169
tgtagtaatg atttgatgat aaag                                              24

<210> SEQ ID NO 170
<211> LENGTH: 24
<212> TYPE: DNA
```

```
<213> ORGANISM: Artificial Sequence
<220> FEATURE:
<223> OTHER INFORMATION: Description of Artificial Sequence:Artificially
      Synthesized DNA Sequence

<400> SEQUENCE: 170
tgaagattgt tattagtgat attg                                          24

<210> SEQ ID NO 171
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 171
gtatttgaat gatgtaatag tgta                                          24

<210> SEQ ID NO 172
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 172
gtatatgatg tattagattg aaag                                          24

<210> SEQ ID NO 173
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 173
aaagttagat tgaaagtgat aaag                                          24

<210> SEQ ID NO 174
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 174
gtaagatgtt gatatagaag atta                                          24

<210> SEQ ID NO 175
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 175
taatatgaga tgaaagtgaa ttag                                          24

<210> SEQ ID NO 176
<211> LENGTH: 24
<212> TYPE: DNA
<213> ORGANISM: Artificial Sequence
```

```
<220> FEATURE:
<223> OTHER INFORMATION: Description of Artificial Sequence:Artificially
      Synthesized DNA Sequence

<400> SEQUENCE: 176
ttagtgaaga agtatagttt attg                                          24

<210> SEQ ID NO 177
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 177
gtagttgaga agatagtaat taat                                          24

<210> SEQ ID NO 178
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 178
atgagatgat atttgagaag taat                                          24

<210> SEQ ID NO 179
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 179
gatgtgaaga agatgaatat atat                                          24

<210> SEQ ID NO 180
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 180
aaagtatagt aagatgtata gtag                                          24

<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 181
gaagtaatat gagtagttga atat                                          24

<210> SEQ ID NO 182
<211> LENGTH: 24
<212> TYPE: DNA
<213> ORGANISM: Artificial Sequence
<220> FEATURE:
```

<223> OTHER INFORMATION: Description of Artificial Sequence:Artificially
      Synthesized DNA Sequence

<400> SEQUENCE: 182
ttgataatgt ttgtttgttt gtag                                          24

<210> SEQ ID NO 183
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 183
tgaagaagaa agtataatga tgaa                                          24

<210> SEQ ID NO 184
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 184
gtagattagt ttgaagtgaa taat                                          24

<210> SEQ ID NO 185
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 185
tatagtagtg aagatgatat atga                                          24

<210> SEQ ID NO 186
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 186
tataatgagt tgttagatat gttg                                          24

<210> SEQ ID NO 187
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 187
gttgtgaaat tagatgtgaa atat                                          24

<210> SEQ ID NO 188
<211> LENGTH: 24
<212> TYPE: DNA
<213> ORGANISM: Artificial Sequence
<220> FEATURE:
<223> OTHER INFORMATION: Description of Artificial Sequence:Artificially -continued Synthesized DNA Sequence

<400> SEQUENCE: 188
taatgttgtg aataatgtag aaag                                          24

<210> SEQ ID NO 189
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 189
gtttatagtg aaatatgaag atag                                          24

<210> SEQ ID NO 190
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 190
attatgaagt aagttaatga gaag                                          24

<210> SEQ ID NO 191
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 191
gatgaaagta atgtttattg tgaa                                          24

<210> SEQ ID NO 192
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 192
attattgaga tgtgaagttt gttt                                          24

<210> SEQ ID NO 193
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 193
tgtagaagat gagatgtata atta                                          24

<210> SEQ ID NO 194
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

```
<400> SEQUENCE: 194
taatttgagt tgtgtatata gtag                                              24

<210> SEQ ID NO 195
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 195
tgatattagt aagaagttga atag                                              24

<210> SEQ ID NO 196
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 196
gttagttatt gagaagtgta tata                                              24

<210> SEQ ID NO 197
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 197
gtagtaatgt taatgaatta gtag                                              24

<210> SEQ ID NO 198
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 198
gtttgtttga tgtgattgaa taat                                              24

<210> SEQ ID NO 199
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 199
gtaagtagta atttgaatat gtag                                              24

<210> SEQ ID NO 200
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence
```

-continued

```
<400> SEQUENCE: 200
gtttgaagat atgtttgaag tata                                          24

<210> SEQ ID NO 201
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 201
atgataattg aagatgtaat gttg                                          24

<210> SEQ ID NO 202
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 202
gtagatagta tagttgtaat gtta                                          24

<210> SEQ ID NO 203
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 203
gatgtgaatg taatatgttt atag                                          24

<210> SEQ ID NO 204
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 204
tgaaattagt ttgtaagatg tgta                                          24

<210> SEQ ID NO 205
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 205
tgtagtataa agtatatgaa gtag                                          24

<210> SEQ ID NO 206
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 206
```
atatgttgtt gagttgatag tata                                          24

<210> SEQ ID NO 207
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 207
attattgagt agaaagatag aaag                                          24

<210> SEQ ID NO 208
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 208
gttgttgaat attgaatata gttg                                          24

<210> SEQ ID NO 209
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 209
atgagaagtt agtaatgtaa atag                                          24

<210> SEQ ID NO 210
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 210
tgaaatgaga agattaatga gttt                                          24

<210> SEQ ID NO 211
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 211
atgtttagtg aaaagttagt attg                                          24

<210> SEQ ID NO 212
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized DNA Sequence

<400> SEQUENCE: 212

```
atgttagtga atagtatagt attg                                        24
```

<210> SEQ ID NO 213
<211> LENGTH: 48
<212> TYPE: DNA
<213> ORGANISM: Artificial Sequence
<220> FEATURE:
<223> OTHER INFORMATION: Description of Artificial Sequence:Artificially
      Synthesized Primer

<400> SEQUENCE: 213

```
gattgtaaga tttgataaag tgtatccagg gaagcgtgtc accgtcgt              48
```

<210> SEQ ID NO 214
<211> LENGTH: 24
<212> TYPE: DNA
<213> ORGANISM: Homo sapiens
<220> FEATURE:
<223> OTHER INFORMATION: Forward primer generated from human p53 tumor
      suppressor gene

<400> SEQUENCE: 214

```
tcatggcgac tgtccagctt tgtg                                        24
```

<210> SEQ ID NO 215
<211> LENGTH: 22
<212> TYPE: DNA
<213> ORGANISM: Artificial Sequence
<220> FEATURE:
<223> OTHER INFORMATION: Description of Artificial Sequence:Artificially
      Synthesized illustrative polynucleotide sequence

<400> SEQUENCE: 215

```
atgttagtga aagttagtat tg                                          22
```

<210> SEQ ID NO 216
<211> LENGTH: 10
<212> TYPE: DNA
<213> ORGANISM: Artificial Sequence
<220> FEATURE:
<223> OTHER INFORMATION: Description of Artificial Sequence:Artificially
      Synthesized illustrative polynucleotide sequence

<400> SEQUENCE: 216

```
gatttgtatt                                                        10
```

<210> SEQ ID NO 217
<211> LENGTH: 10
<212> TYPE: DNA
<213> ORGANISM: Artificial Sequence
<220> FEATURE:
<223> OTHER INFORMATION: Description of Artificial Sequence:Artificially
      Synthesized illustrative polynucleotide sequence

<400> SEQUENCE: 217

```
attgataaag                                                        10
```

POLYNUCLEOTIDES FOR USE AS TAGS AND TAG COMPLEMENTS, MANUFACTURE AND USE THEREOF

CROSS-REFERENCE TO RELATED APPLICATIONS

This application is a continuation of U.S. application Ser. No. 11/729,302, filed Mar. 28, 2007, which is a continuation of U.S. application Ser. No. 10/470,107, now U.S. Pat. No. 7,226,737, which is the U.S. national stage of international patent application PCT/CA02/00087, filed Jan. 25, 2002, which claims the benefit of and priority under 35 U.S.C. §119(e) to U.S. Provisional Patent Application Nos. 60/263,710, filed Jan. 25, 2001, and 60/303,799, filed Jul. 10, 2001, the entire disclosures of each of which are herein incorporated by reference.

FIELD OF THE INVENTION

This invention relates to families of oligonucleotide tags for use, for example, in sorting molecules. Members of a given family of tags can be distinguished one from the other by specific hybridization to their tag complements.

BACKGROUND OF THE INVENTION

Specific hybridization of oligonucleotides and their analogs is a fundamental process that is employed in a wide variety of research, medical, and industrial applications, including the identification of disease-related polynucleotides in diagnostic assays, screening for clones of novel target polynucleotides, identification of specific polynucleotides in blots of mixtures of polynucleotides, therapeutic blocking of inappropriately expressed genes and DNA sequencing. Sequence specific hybridization is critical in the development of high throughput multiplexed nucleic acid assays. As formats for these assays expand to encompass larger amounts of sequence information acquired through projects such as the Human Genome project, the challenge of sequence specific hybridization with high fidelity is becoming increasingly difficult to achieve.

In large part, the success of hybridization using oligonucleotides depends on minimizing the number of false positives and false negatives. Such problems have made the simultaneous use of multiple hybridization probes in a single experiment i.e. multiplexing, particularly in the analysis of multiple gene sequences on a gene microarray, very difficult. For example, in certain binding assays, a number of nucleic acid molecules are bound to a chip with the desire that a given "target" sequence will bind selectively to its complement attached to the chip. Approaches have been developed that involve the use of oligonucleotide tags attached to a solid support that can be used to specifically hybridize to the tag complements that are coupled to probe sequences. Chetverin et al. (WO 93/17126) uses sectioned, binary oligonucleotide arrays to sort and survey nucleic acids. These arrays have a constant nucleotide sequence attached to an adjacent variable nucleotide sequence, both bound to a solid support by a covalent linking moiety. These binary arrays have advantages compared with ordinary arrays in that they can be used to sort strands according to their terminal sequences so that each strand binds to a fixed location on an array. The design of the terminal sequences in this approach comprises the use of constant and variable sequences. U.S. Pat. Nos. 6,103,463 and 6,322,971 issued to Chetverin et al. on Aug. 15, 2000 and Nov. 27, 2001, respectively.

This concept of using molecular tags to sort a mixture of molecules is analogous to molecular tags developed for bacterial and yeast genetics (Hensel et al., Science; 269, 400-403: 1995 and Schoemaker et al., Nature Genetics; 14, 450-456: 1996). Here, a method termed "signature tagged" mutagenesis in which each mutant is tagged with a different DNA sequence is used to recover mutant genes from a complex mixture of approximately 10,000 bacterial colonies. In the tagging approach of Barany et al. (WO 9731256), known as the "zip chip", a family of nucleic acid molecules, the "zipcode addresses", each different from each other, are set out on a grid. Target molecules are attached to oligonucleotide sequences complementary to the "zipcode addresses," referred to as "zipcodes," which are used to specifically hybridize to the address locations on the grid. While the selection of these families of polynucleotide sequences used as addresses is critical for correct performance of the assay, the performance has not been described.

Working in a highly parallel hybridization environment requiring specific hybridization imposes very rigorous selection criteria for the design of families of oligonucleotides that are to be used. The success of these approaches is dependent on the specific hybridization of a probe and its complement. Problems arise as the family of nucleic acid molecules cross-hybridize or hybridize incorrectly to the target sequences. While it is common to obtain incorrect hybridization resulting in false positives or an inability to form hybrids resulting in false negatives, the frequency of such results must be minimized. In order to achieve this goal certain thermodynamic properties of forming nucleic acid hybrids must be considered. The temperature at which oligonucleotides form duplexes with their complementary sequences known as the $T_m$ (the temperature at which 50% of the nucleic acid duplex is dissociated) varies according to a number of sequence dependent properties including the hydrogen bonding energies of the canonical pairs A-T and G-C (reflected in GC or base composition), stacking free energy and, to a lesser extent, nearest neighbour interactions. These energies vary widely among oligonucleotides that are typically used in hybridization assays. For example, hybridization of two probe sequences composed of 24 nucleotides, one with a 40% GC content and the other with a 60% GC content, with its complementary target under standard conditions theoretically may have a 10° C. difference in melting temperature (Mueller et al., Current Protocols in Mol. Biol.; 15, 5: 1993). Problems in hybridization occur when the hybrids are allowed to form under hybridization conditions that include a single hybridization temperature that is not optimal for correct hybridization of all oligonucleotide sequences of a set. Mismatch hybridization of non-complementary probes can occur forming duplexes with measurable mismatch stability (Peyret et al., Biochemistry; 38: 3468-77, 1999). Mismatching of duplexes in a particular set of oligonucleotides can occur under hybridization conditions where the mismatch results in a decrease in duplex stability that results in a higher $T_m$ than the least stable correct duplex of that particular set. For example, if hybridization is carried out under conditions that favor the AT-rich perfect match duplex sequence, the possibility exists for hybridizing a GC-rich duplex sequence that contains a mismatched base having a melting temperature that is still above the correctly formed AT-rich duplex. Therefore design of families of oligonucleotide sequences that can be used in multiplexed hybridization reactions must include consideration for the thermodynamic properties of oligonucleotides and duplex formation that will reduce or eliminate cross hybridization behavior within the designed oligonucleotide set.

A multiplex sequencing method has been described in U.S. Pat. No. 4,942,124, which issued to Church on Jul. 17, 1990. The method requires at least two vectors which differ from each other at a tag sequence. It is stated in the specification that a tag sequence in one vector will not hybridize under stringent hybridization conditions to a tag sequence in another vector, i.e. a complementary probe of a tag in one vector does not cross-hybridize with a tag sequence in another vector. Exemplary stringent hybridization conditions are given as 42° C. in 500-1000 mM sodium phosphate buffer. A set of 42 20-mer tag sequences, all of which lack G residues, is given in FIG. 3 of Church's specification. Details of how the sequences were obtained are not provided, although Church states that initially 92 were chosen on the basis of their having sufficient sequence diversity to insure uniqueness.

There have been other attempts at the development of families of tags. There are a number of different approaches for selecting sequences for use in multiplexed hybridization assays. The selection of sequences that can be used as zipcodes or tags in an addressable array has been described in the patent literature in an approach taken by Brenner and co-workers. U.S. Pat. No. 5,654,413 describes a population of oligonucleotide tags (and corresponding tag complements) in which each oligonucleotide tag includes a plurality of subunits, each subunit consisting of an oligonucleotide having a length of from three to six nucleotides and each subunit being selected from a minimally cross hybridizing set, wherein a subunit of the set would have at least two mismatches with any other sequence of the set. Table II of the Brenner patent specification describes exemplary groups of 4mer subunits that are minimally cross hybridizing according to the aforementioned criteria. In the approach taken by Brenner, constructing non cross-hybridizing oligonucleotides, relies on the use of subunits that form a duplex having at least two mismatches with the complement of any other subunit of the same set. The ordering of subunits in the construction of oligonucleotide tags is not specifically defined.

Parameters used in the design of tags based on subunits are discussed in Barany et al. (WO 9731256). For example, in the design of polynucleotide sequences that are for example 24 nucleotides in length (24mer) derived from a set of four possible tetramers in which each 24mer "address" differs from its, nearest 24mer neighbour by 3 tetramers. They discuss further that, if each tetramer differs from each other by at least two nucleotides, then each 24mer will differ from the next by at least six nucleotides. This is determined without consideration for insertions or deletions when forming the alignment between any two sequences of the set. In this way a unique "zip code" sequence is generated. The zip code is ligated to a label in a target dependent manner, resulting in a unique "zip code" which is then allowed to hybridize to its address on the chip. To minimize cross-hybridization of a "zip code" to other "addresses", the hybridization reaction is carried out at temperatures of 75-80° C. Due to the high temperature conditions for hybridization, 24mers that have partial homology hybridize to a lesser extent than sequences with perfect complementarity and represent 'dead zones'. This approach of implementing stringent hybridization conditions for example, involving high temperature hybridization, is also practiced by Brenner et. al.

The current state of technology for designing non-cross hybridizing tags based on subunits does not provide sufficient guidance to construct a family of sequences with practical value in assays that require stringent non-cross hybridizing behavior.

Thus, while it is desirable with such arrays to have, at once, a large number of address molecules, the address molecules should each be highly selective for its own complement sequence. While such an array provides the advantage that the family of molecules making up the grid is entirely of design, and does not rely on sequences as they occur in nature, the provision of a family of molecules, which is sufficiently large and where each individual member is sufficiently selective for its complement over all the other zipcode molecules (i.e., where there is sufficiently low cross-hybridization, or crosstalk) continues to elude researchers.

SUMMARY OF INVENTION

Using the method of Benight et al. (described in commonly-owned international patent application No. PCT/CA 01/00141 published under WO 01/59151 on Aug. 16, 2001) a family of 100 nucleotide sequences was obtained using a computer algorithm to have optimal hybridization properties for use in nucleic acid detection assays. The sequence set of 100 oligonucleotides was characterized in hybridization assays, demonstrating the ability of family members to correctly hybridize to their complementary sequences with an absence of cross hybridization. These are the sequences having SEQ ID NOs:1 to 100 of Table I. This set of sequences has been expanded to include an additional 110 sequences that can be grouped with the original 100 sequences as having non-cross hybridizing properties, based on the characteristics of the original set of 100 sequences. These additional sequences are identified as SEQ ID NOs:101 to 210 of the sequences in Table I. How these Sequences were Obtained is Described Below.

Variant families of sequences (seen as tags or tag complements) of a family of sequences taken from Table I are also part of the invention. For the purposes of discussion, families of tag complements will be described.

A family of complements is obtained from a set of oligonucleotides based on a family of oligonucleotides such as those of Table I. For illustrative purposes, providing a family of complements based on the oligonucleotides of Table I will be described.

Firstly, sequences based on the oligonucleotides of Table I can be represented as follows:

TABLE IA

Numeric sequences corresponding to word patterns of a set of oligonucleotides

| Sequence Identifier | Numeric Pattern | | | | | |
|---|---|---|---|---|---|---|
| 1 | 1 | 4 | 6 | 6 | 1 | 3 |
| 2 | 2 | 4 | 5 | 5 | 2 | 3 |
| 3 | 1 | 8 | 1 | 2 | 3 | 4 |
| 4 | 1 | 7 | 1 | 9 | 8 | 4 |
| 5 | 1 | 1 | 9 | 2 | 6 | 9 |
| 6 | 1 | 2 | 4 | 3 | 9 | 6 |
| 7 | 9 | 8 | 9 | 8 | 10 | 9 |
| 8 | 9 | 1 | 2 | 3 | 8 | 10 |
| 9 | 8 | 8 | 7 | 4 | 3 | 1 |
| 10 | 1 | 1 | 1 | 1 | 1 | 2 |
| 11 | 2 | 1 | 3 | 3 | 2 | 2 |
| 12 | 3 | 1 | 2 | 2 | 3 | 2 |
| 13 | 4 | 1 | 4 | 4 | 4 | 2 |
| 14 | 1 | 2 | 3 | 3 | 1 | 1 |
| 15 | 1 | 3 | 2 | 2 | 1 | 4 |
| 16 | 3 | 3 | 3 | 3 | 3 | 4 |
| 17 | 4 | 3 | 1 | 1 | 4 | 4 |
| 18 | 3 | 4 | 1 | 1 | 3 | 3 |
| 19 | 3 | 6 | 6 | 6 | 3 | 5 |

TABLE IA-continued

Numeric sequences corresponding to word patterns of a set of oligonucleotides

| Sequence Identifier | Numeric Pattern | | | | | |
|---|---|---|---|---|---|---|
| 20 | 6 | 6 | 1 | 1 | 6 | 5 |
| 21 | 7 | 6 | 7 | 7 | 7 | 5 |
| 22 | 8 | 7 | 5 | 5 | 8 | 8 |
| 23 | 2 | 1 | 7 | 7 | 1 | 1 |
| 24 | 2 | 3 | 2 | 3 | 1 | 3 |
| 25 | 2 | 6 | 5 | 6 | 1 | 6 |
| 26 | 4 | 8 | 1 | 1 | 3 | 8 |
| 27 | 5 | 3 | 1 | 1 | 6 | 3 |
| 28 | 5 | 6 | 8 | 8 | 6 | 6 |
| 29 | 8 | 3 | 6 | 5 | 7 | 3 |
| 30 | 1 | 2 | 3 | 1 | 4 | 6 |
| 31 | 1 | 5 | 7 | 5 | 4 | 3 |
| 32 | 2 | 1 | 6 | 7 | 3 | 6 |
| 33 | 2 | 6 | 1 | 3 | 3 | 1 |
| 34 | 2 | 7 | 6 | 8 | 3 | 1 |
| 35 | 3 | 4 | 3 | 1 | 2 | 5 |
| 36 | 3 | 5 | 6 | 1 | 2 | 7 |
| 37 | 3 | 6 | 1 | 7 | 2 | 7 |
| 38 | 4 | 6 | 3 | 5 | 1 | 7 |
| 39 | 5 | 4 | 6 | 3 | 8 | 6 |
| 40 | 6 | 8 | 2 | 3 | 7 | 1 |
| 41 | 7 | 1 | 7 | 8 | 6 | 3 |
| 42 | 7 | 3 | 4 | 1 | 6 | 8 |
| 43 | 4 | 7 | 7 | 1 | 2 | 4 |
| 44 | 3 | 6 | 5 | 2 | 6 | 3 |
| 45 | 1 | 4 | 1 | 4 | 6 | 1 |
| 46 | 3 | 3 | 1 | 4 | 8 | 1 |
| 47 | 8 | 3 | 3 | 5 | 3 | 8 |
| 48 | 1 | 3 | 6 | 6 | 3 | 7 |
| 49 | 7 | 3 | 8 | 6 | 4 | 7 |
| 50 | 3 | 1 | 3 | 7 | 8 | 6 |
| 51 | 10 | 9 | 5 | 5 | 10 | 10 |
| 52 | 7 | 10 | 10 | 10 | 7 | 9 |
| 53 | 9 | 9 | 7 | 7 | 10 | 9 |
| 54 | 9 | 3 | 10 | 3 | 10 | 3 |
| 55 | 9 | 6 | 3 | 4 | 10 | 6 |
| 56 | 10 | 4 | 10 | 3 | 9 | 4 |
| 57 | 3 | 9 | 3 | 10 | 4 | 9 |
| 58 | 9 | 10 | 5 | 9 | 4 | 8 |
| 59 | 3 | 9 | 4 | 9 | 10 | 7 |
| 60 | 3 | 5 | 9 | 4 | 10 | 8 |
| 61 | 4 | 10 | 5 | 4 | 9 | 3 |
| 62 | 5 | 3 | 3 | 9 | 8 | 10 |
| 63 | 6 | 8 | 6 | 9 | 7 | 10 |
| 64 | 4 | 6 | 10 | 9 | 6 | 4 |
| 65 | 4 | 9 | 8 | 10 | 8 | 3 |
| 66 | 7 | 7 | 9 | 10 | 5 | 3 |
| 67 | 8 | 8 | 9 | 3 | 9 | 10 |
| 68 | 8 | 10 | 2 | 9 | 5 | 9 |
| 69 | 9 | 6 | 2 | 2 | 7 | 10 |
| 70 | 9 | 7 | 5 | 3 | 10 | 6 |
| 71 | 10 | 3 | 6 | 8 | 9 | 2 |
| 72 | 10 | 9 | 3 | 2 | 7 | 3 |
| 73 | 8 | 9 | 10 | 3 | 6 | 2 |
| 74 | 3 | 2 | 5 | 10 | 8 | 9 |
| 75 | 8 | 2 | 3 | 10 | 2 | 9 |
| 76 | 6 | 3 | 9 | 8 | 2 | 10 |
| 77 | 3 | 7 | 3 | 9 | 9 | 10 |
| 78 | 9 | 10 | 1 | 1 | 9 | 4 |
| 79 | 10 | 1 | 9 | 1 | 4 | 1 |
| 80 | 7 | 1 | 10 | 9 | 8 | 1 |
| 81 | 9 | 1 | 10 | 1 | 10 | 6 |
| 82 | 9 | 6 | 9 | 1 | 3 | 10 |
| 83 | 3 | 10 | 8 | 8 | 9 | 1 |
| 84 | 3 | 8 | 1 | 9 | 10 | 3 |
| 85 | 9 | 10 | 1 | 3 | 6 | 9 |
| 86 | 1 | 9 | 1 | 10 | 3 | 1 |
| 87 | 1 | 4 | 9 | 6 | 8 | 10 |
| 88 | 3 | 3 | 9 | 6 | 1 | 10 |
| 89 | 5 | 3 | 1 | 6 | 9 | 10 |
| 90 | 6 | 1 | 8 | 10 | 9 | 6 |
| 91 | 5 | 9 | 9 | 4 | 10 | 3 |
| 92 | 2 | 10 | 9 | 1 | 9 | 5 |
| 93 | 10 | 10 | 7 | 2 | 1 | 9 |
| 94 | 10 | 9 | 9 | 1 | 8 | 2 |
| 95 | 1 | 8 | 6 | 8 | 9 | 10 |
| 96 | 1 | 9 | 1 | 3 | 8 | 10 |
| 97 | 9 | 6 | 9 | 10 | 1 | 2 |
| 98 | 1 | 10 | 8 | 9 | 9 | 2 |
| 99 | 1 | 9 | 6 | 7 | 2 | 9 |
| 100 | 4 | 3 | 9 | 3 | 5 | 1 |
| 101 | 5 | 11 | 10 | 14 | 12 | 1 |
| 102 | 7 | 12 | 4 | 13 | 3 | 2 |
| 103 | 5 | 5 | 4 | 4 | 12 | 9 |
| 104 | 2 | 13 | 13 | 11 | 13 | 13 |
| 105 | 10 | 2 | 5 | 4 | 12 | 7 |
| 106 | 11 | 7 | 4 | 11 | 6 | 4 |
| 107 | 12 | 12 | 1 | 9 | 11 | 11 |
| 108 | 12 | 9 | 4 | 14 | 12 | 6 |
| 109 | 12 | 7 | 13 | 2 | 9 | 11 |
| 110 | 9 | 11 | 3 | 4 | 1 | 3 |
| 111 | 10 | 5 | 12 | 11 | 4 | 4 |
| 112 | 4 | 13 | 7 | 12 | 1 | 5 |
| 113 | 9 | 13 | 10 | 11 | 11 | 6 |
| 114 | 10 | 14 | 14 | 10 | 1 | 3 |
| 115 | 2 | 14 | 1 | 10 | 4 | 5 |
| 116 | 10 | 12 | 12 | 7 | 11 | 10 |
| 117 | 9 | 11 | 2 | 12 | 8 | 11 |
| 118 | 2 | 8 | 5 | 2 | 12 | 14 |
| 119 | 1 | 8 | 13 | 3 | 7 | 8 |
| 120 | 9 | 4 | 7 | 5 | 4 | 2 |
| 121 | 13 | 2 | 12 | 7 | 1 | 12 |
| 122 | 11 | 10 | 9 | 7 | 5 | 11 |
| 123 | 8 | 12 | 2 | 2 | 12 | 7 |
| 124 | 5 | 2 | 14 | 3 | 4 | 13 |
| 125 | 1 | 8 | 8 | 1 | 5 | 9 |
| 126 | 14 | 5 | 11 | 10 | 13 | 3 |
| 127 | 14 | 1 | 4 | 13 | 2 | 4 |
| 128 | 4 | 4 | 5 | 11 | 3 | 10 |
| 129 | 10 | 9 | 2 | 3 | 3 | 11 |
| 130 | 11 | 4 | 8 | 14 | 3 | 4 |
| 131 | 5 | 1 | 14 | 8 | 11 | 2 |
| 132 | 14 | 3 | 11 | 6 | 12 | 5 |
| 133 | 13 | 4 | 4 | 1 | 10 | 1 |
| 134 | 6 | 10 | 11 | 6 | 5 | 1 |
| 135 | 5 | 8 | 12 | 5 | 1 | 7 |
| 136 | 4 | 5 | 9 | 6 | 9 | 2 |
| 137 | 13 | 2 | 4 | 4 | 2 | 3 |
| 138 | 11 | 2 | 2 | 5 | 9 | 3 |
| 139 | 8 | 1 | 10 | 12 | 2 | 8 |
| 140 | 12 | 7 | 9 | 11 | 4 | 1 |
| 141 | 12 | 1 | 4 | 14 | 3 | 13 |
| 142 | 11 | 2 | 7 | 10 | 4 | 1 |
| 143 | 3 | 4 | 12 | 11 | 11 | 11 |
| 144 | 3 | 3 | 4 | 2 | 12 | 11 |
| 145 | 1 | 5 | 9 | 4 | 2 | 1 |
| 146 | 6 | 1 | 12 | 2 | 10 | 5 |
| 147 | 10 | 5 | 1 | 12 | 2 | 14 |
| 148 | 2 | 11 | 7 | 9 | 4 | 11 |
| 149 | 7 | 4 | 4 | 5 | 14 | 12 |
| 150 | 12 | 5 | 2 | 1 | 10 | 12 |
| 151 | 5 | 9 | 2 | 11 | 6 | 1 |
| 152 | 12 | 14 | 3 | 6 | 1 | 14 |
| 153 | 5 | 9 | 11 | 10 | 1 | 4 |
| 154 | 2 | 5 | 12 | 14 | 10 | 10 |
| 155 | 4 | 5 | 8 | 4 | 5 | 6 |
| 156 | 10 | 12 | 4 | 6 | 12 | 5 |
| 157 | 4 | 2 | 1 | 13 | 6 | 8 |
| 158 | 9 | 10 | 10 | 14 | 5 | 3 |
| 159 | 6 | 14 | 10 | 11 | 3 | 3 |
| 160 | 2 | 9 | 10 | 12 | 5 | 7 |
| 161 | 13 | 3 | 7 | 10 | 5 | 12 |
| 162 | 6 | 4 | 1 | 2 | 5 | 13 |
| 163 | 6 | 1 | 13 | 4 | 14 | 13 |
| 164 | 2 | 12 | 1 | 14 | 1 | 9 |
| 165 | 4 | 11 | 13 | 2 | 6 | 10 |

TABLE IA-continued

Numeric sequences corresponding to word patterns of a set of oligonucleotides

| Sequence Identifier | Numeric Pattern | | | | |
|---|---|---|---|---|---|
| 166 | 1 | 10 | 7 | 4 | 5 | 8 |
| 167 | 7 | 2 | 2 | 10 | 13 | 4 |
| 168 | 8 | 2 | 11 | 4 | 6 | 14 |
| 169 | 4 | 8 | 2 | 6 | 2 | 3 |
| 170 | 7 | 1 | 12 | 11 | 2 | 9 |
| 171 | 5 | 6 | 10 | 4 | 13 | 4 |
| 172 | 5 | 10 | 4 | 11 | 9 | 3 |
| 173 | 3 | 11 | 9 | 3 | 2 | 3 |
| 174 | 8 | 15 | 6 | 20 | 17 | 19 |
| 175 | 21 | 10 | 15 | 3 | 7 | 11 |
| 176 | 11 | 7 | 17 | 20 | 14 | 9 |
| 177 | 16 | 6 | 17 | 13 | 21 | 21 |
| 178 | 10 | 15 | 22 | 6 | 17 | 21 |
| 179 | 15 | 7 | 17 | 10 | 22 | 22 |
| 180 | 3 | 20 | 8 | 15 | 20 | 16 |
| 181 | 17 | 21 | 10 | 16 | 6 | 22 |
| 182 | 6 | 21 | 14 | 14 | 14 | 16 |
| 183 | 7 | 17 | 3 | 20 | 10 | 7 |
| 184 | 16 | 19 | 14 | 17 | 7 | 21 |
| 185 | 20 | 16 | 7 | 15 | 22 | 10 |
| 186 | 20 | 10 | 18 | 11 | 22 | 18 |
| 187 | 18 | 7 | 19 | 15 | 7 | 22 |
| 188 | 21 | 18 | 7 | 21 | 16 | 3 |
| 189 | 14 | 13 | 7 | 22 | 17 | 13 |
| 190 | 19 | 7 | 8 | 12 | 10 | 17 |
| 191 | 15 | 3 | 21 | 14 | 9 | 7 |
| 192 | 19 | 6 | 15 | 7 | 14 | 14 |
| 193 | 4 | 17 | 10 | 15 | 20 | 19 |
| 194 | 21 | 6 | 18 | 4 | 20 | 16 |
| 195 | 2 | 19 | 8 | 17 | 6 | 13 |
| 196 | 12 | 12 | 6 | 17 | 4 | 20 |
| 197 | 16 | 21 | 12 | 10 | 19 | 16 |
| 198 | 14 | 14 | 15 | 2 | 7 | 21 |
| 199 | 8 | 16 | 21 | 6 | 22 | 16 |
| 200 | 14 | 17 | 22 | 14 | 17 | 20 |
| 201 | 10 | 21 | 7 | 15 | 21 | 18 |
| 202 | 16 | 13 | 20 | 18 | 21 | 12 |
| 203 | 15 | 7 | 4 | 22 | 14 | 13 |
| 204 | 7 | 19 | 14 | 8 | 15 | 4 |
| 205 | 4 | 5 | 3 | 20 | 7 | 16 |
| 206 | 22 | 18 | 6 | 18 | 13 | 20 |
| 207 | 19 | 6 | 16 | 3 | 13 | 3 |
| 208 | 18 | 6 | 22 | 7 | 20 | 18 |
| 209 | 10 | 17 | 11 | 21 | 8 | 13 |
| 210 | 7 | 10 | 17 | 19 | 10 | 14 |

Here, each of the numerals 1 to 22 (numeric identifiers) represents a 4mer and the pattern of numerals 1 to 22 of the sequences in the above list corresponds to the pattern of tetrameric oligonucleotide segments present in the oligonucleotides of Table I, which oligonucleotides have been found to be non-cross-hybridizing, as described further in the detailed examples. Each 4mer is selected from the group of 4mers consisting of WWWW, WWWX, WWWY, WWXW, WWXX, WWXY, WWYW, WWYX, WWYY, WXWW, WXWX, WXWY, WXXW, WXXX, WXXY, WXYW, WXYX, WXYY, WYWW, WYWX, WYWY, WYXW, WYXX, WYXY, WYYW, WYYX, WYYY, XWWW, XWWX, XWWY, XWXW, XWXX, XWXY, XWYW, XWYX, XWYY, XXWW, XXWX, XXWY, XXXW, XXXX, XXXY, XXYW, XXYX, XXYY, XYWW, XYWX, XYWY, XYXW, XYXX, XYXY, XYYW, XYYX, XYYY, YWWW, YWWX, YWWY, YWXW, YWXX, YWXY, YWYW, YWYX, YWYY, YXWW, YXWX, YXWY, YXXW, YXXX, YXXY, YXYW, YXYX, YXYY, YYWW, YYWX, YYWY, YYXW, YYXX, YYXY, YYYW, YYYX, and YYYY. Here W, X and Y represent nucleotide bases, A, G, C, etc., the assignment of bases being made according to rules described below.

Given this numeric pattern, a 4mer is assigned to a numeral. For example, 1=WXYY, 2=YWXY, etc. Once a given 4mer has been assigned to a given numeral, it is not assigned for use in the position of a different numeral. It is possible, however, to assign a different 4mer to the same numeral. That is, for example, the numeral 1 in one position could be assigned WXYY and another numeral 1, in a different position, could be assigned XXXW, but none of the other numerals 2 to 10 can then be assigned WXYY or XXXW. A different way of saying this is that each of 1 to 22 is assigned a 4mer from the list of eighty-one 4mers indicated so as to be different from all of the others of 1 to 22.

In the case of the specific oligonucleotides given in Table I, 1=WXYY, 2=YWXY, 3=XXXW, 4=YWYX, 5=WYXY, 6=YYWX, 7=YWXX, 8=WYXX, 9=XYYW, 10=XYWX, 11=YYXW, 12=WYYX, 13=XYXW, 14=WYYY, 15=WXYW, 16=WYXW, 17=WXXW, 18=WYYW, 19=XYYX, 20=YXYX, 21=YXXY and 22=XYXY.

Once the 4mers are assigned to positions according to the above pattern, a particular set of oligonucleotides can be created by appropriate assignment of bases, A, T/U, G, C to W, X, Y. These assignments are made according to one of the following two sets of rules:

(i) Each of W, X and Y is a base in which:
 (a) W=one of A, T/U, G, and C,
  X=one of A, T/U, G, and C,
  Y=one of A, T/U, G, and C,
  and each of W, X and Y is selected so as to be different from all of the others of W, X and Y, and
 (b) an unselected said base of (i)(a) can be substituted any number of times for any one of W, X and Y.

or (ii) Each of W, X and Y is a base in which:
 (a) W=G or C,
  X=A or T/U,
  Y=A or T/U,
  and X≠Y, and
 (b) a base not selected in (ii)(a) can be inserted into each sequence at one or more locations, the location of each insertion being the same in each sequence as that of every other sequence of the set.

In the case of the specific oligonucleotides given in Table I, W=G, X=A and Y=T.

In any case, given a set of oligonucleotides generated according to one of these sets of rules, it is possible to modify the members of a given set in relatively minor ways and thereby obtain a different set of sequences while more or less maintaining the cross-hybridization properties of the set subject to such modification. In particular, it is possible to insert up to 3 of A, T/U, G and C at any location of any sequence of the set of sequences. Alternatively, or additionally, up to 3 bases can be deleted from any sequence of the set of sequences.

A person skilled in the art would understand that given a set of oligonucleotides having a set of properties making it suitable for use as a family of tags (or tag complements) one can obtain another family with the same property by reversing the order of all of the members of the set. In other words, all the members can be taken to be read 5' to 3' or to be read 3' to 5'.

A family of complements of the present invention is based on a given set of oligonucleotides defined as described above. Each complement of the family is based on a different oligonucleotide of the set and each complement contains at least 10 consecutive (i.e., contiguous) bases of the oligonucleotide on which it is based. When selecting a sequence of contiguous bases, preference is given to those sets in which the contiguous bases of each oligonucleotide of a set are selected such that the position of the first base of each said oligonucleotide within the sequence on which it is based is the same for all nucleotides of the set. Thus, for example, if a nucleotide sequence of twenty contiguous bases corresponds to bases 3 to 22 of the sequence on which the nucleotide sequence is based, then preferably, the twenty contiguous bases for all nucleotide sequences corresponds to bases 3 to 22 of the sequences on which the nucleotides sequences are based. For a given family of complements where one is seeking to reduce or minimize inter-sequence similarity that would result in cross-hybridization, each and every pair of complements meets particular homology requirements. Particularly, subject to limited exceptions, described below, any two complements within a set of complements are generally required to have a defined amount of dissimilarity.

In order to notionally understand these requirements for dissimilarity as they exist for a given pair of complements of a family, a phantom sequence is generated from the pair of complements. A "phantom" sequence is a single sequence that is generated from a pair of complements by selection, from each complement of the pair, of a string of bases wherein the bases of the string occur in the same order in both complements. An object of creating such a phantom sequence is to create a convenient and objective means of comparing the sequence identity of the two parent sequences from which the phantom sequence is created.

A phantom sequence can be considered to be similar in concept to a consensus sequence which a person skilled in the art would be familiar with, except that a consensus sequence typically is comprised of all bases from both parent sequences with each position reflecting the most common choice of base at each position (the union of both sequences), whereas the "phantom" sequence is comprised of only bases which occur in the same order in both parent sequences (the intersection of both sequences). Also, a consensus sequence usually is indicative of a common phylogenetic ancestry for the two sequences (or more than 2 sequences depending on how many sequences are used to generate the consensus sequence), whereas the "phantom" sequence definition has been created to specifically address the sequence similarity between 2 complementary sequences which have no ancestral history but may have a propensity to cross-hybridize under certain conditions.

A phantom sequence may thus be generated from exemplary Sequence 1 and Sequence 2 as follows:

```
                                    (SEQ ID NO: 211)
Sequence 1:         ATGTTTAGTGAAAAGTTAGTATTG
                       *          •

(SEQ ID NO: 212)
Sequence 2:         ATGTTAGTGAATAGTATAGTATTG
                                •  ♦

(SEQ ID NO: 215)
Phantom Sequence:   ATGTTAGTGAAAGTTAGTATTG
```

The phantom sequence generated from these two sequences is thus 22 bases in length. That is, one can see that there are 22 identical bases with identical sequence (the same order) in Sequence Nos. 1 and 2. There is a total of three insertions/deletions and mismatches present in the phantom sequence when compared with the sequences from which it was generated:

```
ATGT-TAGTGAA-AGT-TAGTATTG    (SEQ ID NO: 215)
```

The dashed lines in this latter representation of the phantom sequence indicate the locations of the insertions/deletions and mismatches in the phantom sequence relative to the parent sequences from which it was derived. Thus, the "T" marked with an asterisk in Sequence 1, the "A" marked with a diamond in Sequence 2 and the "A-T" mismatch of Sequences 1 and 2 marked with two dots were deleted in generating the phantom sequence.

A person skilled in the art will appreciate that the term "insertion/deletion" is intended to cover the situations indicated by the asterisk and diamond. Whether the change is considered, strictly speaking, an insertion or deletion is merely one of vantage point. That is, one can see that the fourth base of Sequence 1 can be deleted therefrom to obtain the phantom sequence, or a "T" can be inserted after the third base of the phantom sequence to obtain Sequence 1.

One can thus see that if it were possible to create a phantom sequence by elimination of a single insertion/deletion from one of the parent sequences, that the two parent sequences would have identical homology over the length of the phantom sequence except for the presence of a single base in one of the two sequences being compared. Likewise, one can see that if it were possible to create a phantom sequence through deletion of a mismatched pair of bases, one base in each parent, that the two parent sequences would have identical homology over the length of the phantom sequence except for the presence of a single base in each of the sequences being compared. For this reason, the effect of an insertion/deletion is considered equivalent to the effect of a mismatched pair of bases when comparing the homology of two sequences.

Once a phantom sequence is generated, the compatibility of the pair of complements from which it was generated within a family of complements can be systematically evaluated.

According to one embodiment of the invention, a pair of complements is compatible for inclusion within a family of complements if any phantom sequence generated from the pair of complements has the following properties:

(1) Any consecutive sequence of bases in the phantom sequence which is identical to a consecutive sequence of bases in each of the first and second complements from which it is generated is no more than (($3⁄4$×L)−1) bases in length;

(2) The phantom sequence, if greater than or equal to ($5⁄6$×L) in length, contains at least 3 insertions/deletions or mismatches when compared to the first and second complements from which it is generated; and (3) The phantom sequence is not greater than or equal to ($11⁄12$×L) in length.

Here, $L_1$ is the length of the first complement, $L_2$ is the length of the second complement, and $L=L_1$, or if $L_1 \neq L_2$, L is the greater of $L_1$ and $L_2$.

In particular preferred embodiments of the invention, all pairs of complements of a given set have the properties set out above. Under particular circumstances, it may be advantageous to have a limited number of complements that do not meet all of these requirements when compared to every other complement in a family.

In one case, for any first complement there are at most two second complements in the family which do not meet all of the three listed requirements. For two such complements, there would thus be a greater chance of cross-hybridization between their tag counterparts and the first complement. In another case, for any first complement there is at most one second complement which does not meet all of three listed requirements.

It is also possible, given this invention, to design a family of complements where a specific number or specific portion of the complements do not meet the three listed requirements. For example, a set could be designed where only one pair of complements within the set do not meet the requirements when compared to each other. There could be two pairs, three pairs, and any number of pairs up to and including all possible pairs. Alternatively, it may be advantageous to have a given proportion of pairs of complements that do not meet the requirements, say 10% of pairs, when compared with other sequences that do not meet one or more of the three requirements listed. This number could instead be 5%, 15%, 20%, 25%, 30%, 35%, or 40%.

The foregoing comparisons would generally be largely carried out using appropriate computer software. Although notionally described in terms of a phantom sequence for the sake of clarity and understanding, it will be understood that a competent computer programmer can carry out pairwise comparisons of complements in any number of ways using logical steps that obtain equivalent results.

The symbols A, G, T/U, C take on their usual meaning in the art here. In the case of T and U, a person skilled in the art would understand that these are equivalent to each other with respect to the inter-strand hydrogen-bond (Watson-Crick) binding properties at work in the context of this invention. The two bases are thus interchangeable and hence the designation of T/U.

Analogues of the naturally occurring bases can be inserted in their respective places where desired. An Analogue is any non-natural base, such as Peptide nucleic acids and the like that undergoes normal Watson-Crick pairing in the same way as the naturally occurring nucleotide base to which it corresponds.

In one broad aspect, the present invention is thus a composition comprising molecules for use as tags or tag complements wherein each molecule comprises an oligonucleotide selected from a set of oligonucleotides based on a group of sequences having numeric patters as set out in Table IA wherein:

(A) each of 1 to 22 is a 4mer selected from the group of 4mers consisting of WWWW, WWWX, WWWY, WWXW, WWXX, WWXY, WWYW, WWYX, WWYY, WXWW, WXWX, WXWY, WXXW, WXXX, WXXY, WXYW, WXYX, WXYY, WYWW, WYWX, WYWY, WYXW, WYXX, WYXY, WYYW, WYYX, WYYY, XWWW, XWWX, XWWY, XWXW, XWXX, XWXY, XWYW, XWYX, XWYY, XXWW, XXWX, XXWY, XXXW, XXXX, XXXY, XXYW, XXYX, XXYY, XYWW, XYWX, XYWY, XYXW, XYXX, XYXY, XYYW, XYYX, XYYY, YWWW, YWWX, YWWY, YWXW, YWXX, YWXY, YWYW, YWYX, YWYY, YXWW, YXWX, YXWY, YXXW, YXXX, YXXY, YXYW, YXYX, YXYY, YYWW, YYWX, YYWY, YYXW, YYXX, YYXY, YYYW, YYYX, and YYYY, and (B) each of 1 to 22 is selected so as to be different from all of the others of 1 to 22;

(C) each of W, X and Y is a base in which either (i) or (ii) is true:
  (i) (a) W=one of A, T/U, G, and C,
      X=one of A, T/U, G, and C,
      Y=one of A, T/U, G, and C,
      and each of W, X and Y is selected so as to be different from all of the others of W, X and Y, and
  (b) an unselected said base of (i) (a) can be substituted any number of times for any one of W, X and Y,
  (ii) (a) W=G or C,
      X=A or T/U,
      Y=A or T/U,
      and X≠Y, and
  (b) a base not selected in (ii)(a) can be inserted into each sequence at one or more locations, the location of each insertion being the same in all the sequences;

(D) up to three bases can be inserted at any location of any of the sequences or up to three bases can be deleted from any of the sequences;

(E) all of the sequences of a said group of oligonucleotides are read 5' to 3' or are read 3' to 5'; and wherein each oligonucleotide of a said set has a sequence of at least ten contiguous bases of the sequence on which it is based, provided that:

(F) (I) the quotient of the sum of G and C divided by the sum of A, T/U, G and C for all combined sequences of the set is between about 0.1 and 0.40 and said quotient for each sequence of the set does not vary from the quotient for the combined sequences by more than 0.2; and (II) for any phantom sequence generated from any pair of first and second sequences of the set $L_1$ and $L_2$ in length, respectively, by selection from the first and second sequences of identical bases in identical sequence with each other:
    (i) any consecutive sequence of bases in the phantom sequence which is identical to a consecutive sequence of bases in each of the first and second sequence from which it is generated is less than $((¾×L)-1)$ bases in length;
    (ii) the phantom sequence, if greater than or equal to $(⅚×L)$ in length, contains at least three insertions/deletions or mismatches when compared to the first and second sequences from which it is generated; and
    (iii) the phantom sequence is not greater than or equal to $(11/12×L)$ in length;
    where $L=L_1$, or if $L_1 \neq L_2$, where L is the greater of $L_1$ and $L_2$; and wherein any base present may be substituted by an analogue thereof.

In a preferred embodiment, a set of oligonucleotides of the invention is based on the numeric patters of sequences tested in Example 2.

Preferably, (G) for the group of 24mer sequences in which each 1=GATT, each 2=TGAT, each 3=AAAG, each 4=TGTA, each 5=GTAT, each 6=TTGA, each 7=TGAA, each 8=GTAA, each 9=ATTG, each 10=ATGA, each 11=TTAG, each 12=GTTA, each 13=ATAG, each 14=GTTT, each 15=GATG, each 16=GTAG, each 17=GAAG, each 18=GTTG, each 19=ATTA, each 20=TATA, each 21=TAAT and each 22=ATAT, for the group of sequences in which each 1=GATT, each 2=TGAT, each 3=AAAG, each 4=TGTA, each 5=GTAT, each 6=TTGA, each 7=TGAA, each 8=GTAA, each 9=ATTG, each 10=ATGA, each 11=TTAG, each 12=GTTA, each 13=ATAG, each 14=GTTT, each 15=GATG, each 16=GTAG, each 17=GAAG, each 18=GTTG, each 19=ATTA, each 20=TATA, each 21=TAAT and each 22=ATAT, under a defined set of conditions in which the maximum degree of hybridization between a sequence and any complement of a different sequence of the group of 24mer sequences does not exceed 30% of the degree of hybridization between said sequence and its complement, for all oligonucleotides of the set, the maximum degree of hybridization between an oligonucleotide and a complement of any other oligonucleotide of the set does not exceed 50% of the degree of hybridization of the oligonucleotide and its complement.

It can thus be seen that it is possible to routinely determine whether all oligonucleotides of a selected set are all minimally cross-hybridizing. Preferably in (G), under said defined set of conditions in which the maximum degree of hybridization between a sequence and any complement of a different sequence does not exceed 30% of the degree of hybridization between said sequence and its complement, it is also true that the degree of hybridization between each sequence and its complement varies by a factor of between 1 and 10, more preferably between 1 and 9, and more preferably between 1 and 8. It is demonstrated in Example 2, below, for a preferred set of oligonucleotides, that the degree of hybridization between each sequence and its specific complement varies by a factor of between 1 and 8.25 and the maximum degree of hybridization between a sequence and any complement of a different sequence does not exceed 10.2% of the degree of hybridization between the sequence and its specific complement.

Preferably, the maximum degree of hybridization in (G) between a sequence and any complement of a different sequence of the group of 24mer sequences does not exceed 25%, more preferably wherein the maximum degree of hybridization in (G) between a sequence and any complement of a different sequence of the group of 24mer sequences does not exceed 20%, more preferably wherein the maximum degree of hybridization in (G) between a sequence and any complement of a different sequence of the group of 24mer sequences does not exceed 15%, more preferably wherein the maximum degree of hybridization in (G) between a sequence and any complement of a different sequence of the group of 24mer sequences does not exceed 11%.

Preferably, under the defined set of conditions of (G), the maximum degree of hybridization between a sequence and a complement of any other sequence of the set is no more than 15% greater than the maximum degree of hybridization between a sequence and any complement of a different sequence of the said group of 24mer sequences, more preferably no more than 10% greater, more preferably no more than 5% greater.

According to Example 2, described below, under conditions of 0.2 M NaCl, 0.1 M Tris, 0.08% Triton X-100, pH 8.0 at 37° C., the maximum degree of hybridization between a sequence and any complement of a different sequence of the group of 24mer sequences does not exceed 10.2% when 24mer nucleotide sequences are covalently linked to a solid support, in this case microparticles or beads.

In another preferred aspect of the composition, in (G) for the group of 24mers the maximum degree of hybridization between a sequence and any complement of a different sequence does not exceed 15% of the degree of hybridization between said sequence and its complement and the degree of hybridization between each sequence and its complement varies by a factor of between 1 and 9, and for all oligonucleotides of the set, the maximum degree of hybridization between an oligonucleotide and a complement of any other oligonucleotide of the set does not exceed 20% of the degree of hybridization of the oligonucleotide and its complement.

In a preferred aspect, each of the 4mers represented by numerals 1 to 22 is selected from the group of 4mers consisting of WXXX, WXXY, WXYX, WXYY, WYXX, WYXY, WYYX, WYYY, XWXX, XWXY, XWYX, XWYY, XXWX, XXWY, XXXW, XXYW, XYWX, XYWY, XYXW, XYYW, YWXX, YWXY, YWYX, YWYY, YXWX, YXWY, YXXW, YXYW, YYWX, YYWY, YYXW, and YYYW.

In another aspect, each of the 4mers represented by numeral 1 are identical to each other, each of the 4mers represented by numeral 2 are identical to each other, each of the 4mers represented by numeral 3 are identical to each other, each of the 4mers represented by numeral 4 are identical to each other, each of the 4mers represented by numeral 5 are identical to each other, each of the 4mers represented by numeral 6 are identical to each other, each of the 4mers represented by numeral 7 are identical to each other, each of the 4mers represented by numeral 8 are identical to each other, each of the 4mers represented by numeral 9 are identical to each other, each of the 4mers represented by numeral 10 are identical to each other, each of the 4mers represented by numeral 11 are identical to each other, each of the 4mers represented by numeral 12 are identical to each other, each of the 4mers represented by numeral 13 are identical to each other, each of the 4mers represented by numeral 14 are identical to each other, each of the 4mers represented by numeral 15 are identical to each other, each of the 4mers represented by numeral 16 are identical to each other, each of the 4mers represented by numeral 17 are identical to each other, each of the 4mers represented by numeral 18 are identical to each other, each of the 4mers represented by numeral 19 are identical to each other, each of the 4mers represented by numeral 20 are identical to each other, each of the 4mers represented by numeral 21 are identical to each other, and each of the 4mers represented by numeral 22 are identical to each other.

In another aspect, at least one of the 4mers represented by the numeral 1 has the sequence WXYY, at least one of the 4mers represented by the numeral 2 has the sequence YWXY, at least one of the 4mers represented by the numeral 3 has the sequence XXXW, at least one of the 4mers represented by the numeral 4 has the sequence YWYX, at least one of the 4mers represented by the numeral 5 has the sequence WYXY, at least one of the 4mers represented by the numeral 6 has the sequence YYWX, at least one of the 4mers represented by the numeral 7 has the sequence YWXX, at least one of the 4mers represented by the numeral 8 has the sequence WYXX, at least one of the 4mers represented by the numeral 9 has the sequence XYYW, at least one of the 4mers represented by the numeral 10 has the sequence XYWX, at least one of the 4mers represented by the numeral 11 has the sequence YYXW, at least one of the 4mers represented by the numeral 12 has the sequence WYYX, at least one of the 4mers represented by the numeral 13 has the sequence XYXW, at least one of the 4mers represented by the numeral 14 has the sequence WYYY, at least one of the 4mers represented by the numeral 15 has the sequence WXYW, at least one of the 4mers represented by the numeral 16 has the sequence WYXW, at least one of the 4mers represented by the numeral 17 has the sequence WXXW, at least one of the 4mers represented by the numeral 18 has the sequence WYYW, at least one of the 4mers represented by the numeral 19 has the sequence XYYX, at least one of the 4mers represented by the numeral 20 has the sequence YXYX, at least one of the 4mers represented by the numeral 21 has the sequence YXXY, and/or at least one of the 4mers represented by the numeral 22 has the sequence XYXY.

In one preferred aspect, the invention is a composition in which each 1=WXYY, each 2=YWXY, each 3=XXXW, each 4=YWYX, each 5=WYXY, each 6=YYWX, each 7=YWXX, each 8=WYXX, each 9=XYYW, each 10=XYWX, each 11=YYXW, each 12=WYYX, each 13=XYXW, each 14=WYYY, each 15=WXYW, each 16=WYXW, each 17=WXXW, each 18=WYYW, each 19=XYYX, each 20=YXYX, each 21=YXXY and each 22=XYXY.

In one broad aspect, the invention is a composition wherein a group of sequences is based on those having numeric patterns of those with numeric identifiers 1 to 173 of Table IA and wherein each of the 4mers represented by numerals 1 to 14 in (A) is selected from the group of 4mers consisting of WXYY, YWXY, XXXW, YWYX, WYXY, YYWX, YWXX, WYXX, XYYW, XYWX, YYXW, WYYX, XYXW, and WYYY.

In such a composition it is preferred that each of the 4mers represented by numeral 1 are identical to each other, each of the 4mers represented by numeral 2 are identical to each other, each of the 4mers represented by numeral 3 are identical to each other, each of the 4mers represented by numeral 4 are identical to each other, each of the 4mers represented by numeral 5 are identical to each other, each of the 4mers represented by numeral 6 are identical to each other, each of the 4mers represented by numeral 7 are identical to each other, each of the 4mers represented by numeral 8 are identical to each other, each of the 4mers represented by numeral 9 are identical to each other, each of the 4mers represented by numeral 10 are identical to each other, each of the 4mers represented by numeral 11 are identical to each other, each of the 4mers represented by numeral 12 are identical to each other, each of the 4mers represented by numeral 13 are identical to each other, and/or each of the 4mers represented by numeral 14 are identical to each other.

It is also preferred that at least one of the 4mers represented by the numeral 1 has the sequence WXYY, at least one of the 4mers represented by the numeral 2 has the sequence YWXY, at least one of the 4mers represented by the numeral 3 has the sequence XXXW, at least one of the 4mers represented by the numeral 4 has the sequence YWYX, at least one of the 4mers represented by the numeral 5 has the sequence WYXY, at least one of the 4mers represented by the numeral 6 has the sequence YYWX, at least one of the 4mers represented by the numeral 7 has the sequence YWXX, at least one of the 4mers represented by the numeral 8 has the sequence WYXX, at least one of the 4mers represented by the numeral 9 has the sequence XYYW, at least one of the 4mers represented by the numeral 10 has the sequence XYWX, at least one of the 4mers represented by the numeral 11 has the sequence YYXW, at least one of the 4mers represented by the numeral 12 has the sequence WYYX, at least one of the 4mers represented by the numeral 13 has the sequence XYXW, and/or at least one of the 4mers represented by the numeral 14 has the sequence WYYY.

More preferably, each 1=WXYY, each 2=YWXY, each 3=XXXW, each 4=YWYX, each 5=WYXY, each 6=YYWX, each 7=YWXX, each 8=WYXX, each 9=XYYW, each 10=XYWX, each 11=YYXW, each 12=WYYX, each 13=XYXW, and each 14=WYYY.

In another broad aspect, the invention is a composition in which a group of sequences is based on those sequences having the numeric patters of those with sequence identifiers 1 to 100 set out in Table IA and wherein each of the 4mers represented by numerals 1 to 10 in (A) is selected from the group of 4mers consisting of WXYY, YWXY, XXXW, YWYX, WYXY, YYWX, YWXX, WYXX, XYYW, and XYWX.

In such a composition it is preferred that each of the 4mers represented by numeral 1 are identical to each other, each of the 4mers represented by numeral 2 are identical to each other, each of the 4mers represented by numeral 3 are identical to each other, each of the 4mers represented by numeral 4 are identical to each other, each of the 4mers represented by numeral 5 are identical to each other, each of the 4mers represented by numeral 6 are identical to each other, each of the 4mers represented by numeral 7 are identical to each other, each of the 4mers represented by numeral 8 are identical to each other, each of the 4mers represented by numeral 9 are identical to each other, and/or each of the 4mers represented by numeral 10 are identical to each other.

It also preferred that at least one of the 4mers represented by the numeral 1 has the sequence WXYY, at least one of the 4mers represented by the numeral 2 has the sequence YWXY, at least one of the 4mers represented by the numeral 3 has the sequence XXXW, at least one of the 4mers represented by the numeral 4 has the sequence YWYX, at least one of the 4mers represented by the numeral 5 has the sequence WYXY, at least one of the 4mers represented by the numeral 6 has the sequence YYWX, at least one of the 4mers represented by the numeral 7 has the sequence YWXX, at least one of the 4mers represented by the numeral 8 has the sequence WYXX, at least one of the 4mers represented by the numeral 9 has the sequence XYYW, and/or at least one of the 4mers represented by the numeral 10 has the sequence XYWX.

More preferably, each 1=WXYY, each 2=YWXY, each 3=XXXW, each 4=YWYX, each 5=WYXY, each 6=YYWX, each 7=YWXX, each 8=WYXX, each 9=XYYW, and each 10=XYWX.

In the moat preferred compositions, in (C)(i)(a): W=one of G and C; X=one of A and T/U; and Y=one of A and T/U, maintaining the provisos of (F). More preferably, (C)(i)(a): W=G; X=one of A, and T/U; and Y=one of A and T/U. Even more preferably, wherein W=G; X=A; and Y=T/U.

A person skilled in the art will appreciate that the closer a given oligonucleotide sequence variant is to one of the most preferred sequences (Table I), the more closely it will resemble the preferred sequence as a member of a minimally cross-hybridizing set of oligonucleotides.

It will be understood that when it is stated herein that a group of sequences (oligonucleotides) is minimally cross-hybridizing, it is meant that any given member of the group of sequences (oligonucleotides) only minimally hybridizes with the complement of any other sequence (oligonucleotide) of that group.

Preferably, in (F)(I), the quotient for each sequence of the set does not vary from the quotient for the combined sequences by more than 0.1, more preferably, the quotient for each sequence of the set does not vary from the quotient for the combined sequences by more than 0.05, more preferably the quotient for each sequence of the set does not vary from the quotient for the combined sequences by more than 0.01.

Also, it is preferred in (F)(I) that the quotient of the sum of G and C divided by the sum of A, T/U, G and C for all combined sequences of the set is between about 0.15 and 0.35, more preferably between about 0.2 and 0.3, more preferably between about 0.21 and 0.29, more preferably between about 0.22 and 0.28, more preferably between about 0.23 and 0.27, even more preferably between about 0.24 and 0.26, and most preferably the quotient is 0.25.

Preferably, in (D) up to two bases can be inserted at any location of any of the sequences or up to two bases can be deleted from any of the sequences, more preferably only one base can be inserted at any location of any of the sequences or one base can be deleted from any of the sequences, and most preferably no base is inserted at any location of any of the sequences.

Also, it is preferred that in (D), no base can be deleted from any of the sequences, and most preferably, in (D) no base can be inserted at or deleted from any location of any of the sequences.

In preferred compositions, each of the oligonucleotides of a set has a sequence at least eleven contiguous bases of the sequence on which it is based; or more preferably each of the oligonucleotides of a set has a sequence at least twelve contiguous bases of the sequence on which it is based; or more preferably each of the oligonucleotides of a set has a sequence at least thirteen contiguous bases of the sequence on which it is based; or more preferably each of the oligonucleotides of a set has a sequence at least fourteen contiguous bases of the sequence on which it is based; or more preferably each of the oligonucleotides of a set has a sequence at least fifteen contiguous bases of the sequence on which it is based; or more preferably each of the oligonucleotides of a set has a sequence at least sixteen contiguous bases of the sequence on which it is based; or more preferably each of the oligonucleotides of a set has a sequence at least seventeen contiguous bases of the sequence on which it is based; or more preferably each of the oligonucleotides of a set has a sequence at least eighteen contiguous bases of the sequence on which it is based; or more preferably each of the oligonucleotides of a set has a sequence at least nineteen contiguous bases of the sequence on which it is based; or more preferably each of the oligonucleotides of a set has a sequence at least twenty contiguous bases of the sequence on which it is based; or more preferably each of the oligonucleotides of a set has a sequence at least twenty-one contiguous bases of the sequence on which it is based; or more preferably each of the oligonucleotides of a set has a sequence at least twenty-two contiguous bases of the sequence on which it is based; or more preferably each of the oligonucleotides of a set has a sequence at least twenty-three contiguous bases of the sequence on which it is based; or more preferably each of the oligonucleotides of a set has a sequence at least twenty-four contiguous bases of the sequence on which it is based.

Preferably, each of the oligonucleotides of a set is up to thirty bases in length; or more preferably each of the oligonucleotides of a set is up to twenty-nine bases in length; or more preferably each of the oligonucleotides of a set is up to twenty-eight bases in length; or more preferably each of the oligonucleotides of a set is up to twenty-seven bases in length; or more preferably each of the oligonucleotides of a set is up to twenty-six bases in length; or more preferably each of the oligonucleotides of a set is up to twenty-five bases in length; or more preferably each of the oligonucleotides of a set is up to twenty-four bases in length.

In certain preferred embodiments, each of the oligonucleotides of a set has a length of within five bases of the average length of all of the oligonucleotides in the set; or more preferably each of the oligonucleotides of a set has a length of within four bases of the average length of all of the oligonucleotides in the set; or more preferably each of the oligonucleotides of a set has a length of within three bases of the average length of all of the oligonucleotides in the set; or more preferably each of the oligonucleotides of a set has a length of within two bases of the average length of all of the oligonucleotides in the set; or more preferably each of the oligonucleotides of a set has a length of within one base of the average length of all of the oligonucleotides in the set.

Preferably, the string of contiguous bases of each oligonucleotide of a said set are selected such that the position of the first base of each string within the sequence on which it is based is the same for all nucleotides of the set.

In preferred embodiments, the composition includes at least ten said molecules, or at least eleven said molecules, or at least twelve said molecules, or at least thirteen said molecules, or at least fourteen said molecules, or at least fifteen said molecules, or at least sixteen said molecules, or at least seventeen said molecules, or at least eighteen said molecules, or at least nineteen said molecules, or at least twenty said molecules, or at least twenty-one said molecules, or at least twenty-two said molecules, or at least twenty-three said molecules, or at least twenty-four said molecules, or at least twenty-five said molecules, or at least twenty-six said molecules, or at least twenty-seven said molecules, or at least twenty-eight said molecules, or at least twenty-nine said molecules, or at least thirty said molecules, or at least thirty-one said molecules, or at least thirty-two said molecules, or at least thirty-three said molecules, or at least thirty-four said molecules, or at least thirty-five said molecules, or at least thirty-six said molecules, or at least thirty-seven said molecules, or at least thirty-eight said molecules, or at least thirty-nine said molecules, or at least forty said molecules, or at least forty-one said molecules, or at least forty-two said molecules, or at least forty-three said molecules, or at least forty-four said molecules, or at least forty-five said molecules, or at least forty-six said molecules, or at least forty-seven said molecules, or at least forty-eight said molecules, or at least forty-nine said molecules, or at least fifty said molecules, or at least sixty said molecules, or at least seventy said molecules, or at least eighty said molecules, or at least ninety said molecules, or at least one hundred said molecules, or at least, depending upon the size of the group of sequences on which the oligonucleotides are based, one hundred and ten said molecules, or at least one hundred and twenty said molecules, or at least one hundred and thirty said molecules, or at least one hundred and forty said molecules, or at least one hundred and fifty said molecules, or at least one hundred and sixty said molecules, or at least one hundred and seventy said molecules, or at least one hundred and eighty said molecules, or at least one hundred and ninety said molecules, or at least two hundred said molecules.

A person skilled in the art will appreciate that, depending upon the use to which a family of oligonucleotides of the invention are to be put, it may or may not be desirable to include with sequences that can be distinguished one from the other (i.e., are minimally cross-hybridizing) a number of sequences that do cross hybridize with each other.

In a preferred aspect, the invention is a composition wherein in (II)(i), any consecutive sequence of bases in the phantom sequence which is identical to a consecutive sequence of bases in each of the first and second sequences from which it is generated is no more than $((\frac{2}{3} \times L) - 1)$ bases in length. More preferably, the phantom sequence, if greater than or equal to $(\frac{3}{4} \times L)$ in length, contains at least 3 insertions/deletions or mismatches when compared to the first and second sequences from which it is generated, and even more preferably, the phantom sequence, if greater than or equal to $(\frac{2}{3} \times L)$ in length, contains at least 3 insertions/deletions or mismatches when compared to the first and second sequences from which it is generated.

In another preferred aspect, in (II)(iii), the phantom sequence is not greater than or equal to $(\frac{5}{6} \times L)$ in length, more preferably, the phantom sequence is not greater than or equal to $(\frac{3}{4} \times L)$ in length.

In another broad aspect, the invention is a composition containing molecules for use as tags or tag complements wherein each molecule comprises an oligonucleotide selected from a set of oligonucleotides based on a group of sequences having the numeric patterns of the sequences tested in Example 2, as set out in Table IA, wherein:
(A) wherein 1=WXYY, each 2 YWXY, each 3=XXXW, each 4=YWYX, each 5=WYXY, each 6=YYWX, each 7=YWXX, each 8=WYXX, each 9=XYYW, each 10=XYWX, each 11=YYXW, each 12=WYYX, each 13=XYXW, each 14=WYYY, each 15=WXYW, each 16=WYXW, each 17=WXXW, each 18=WYYW, each 19=XYYX, each 20=YXYX, each 21=YXXY and each 22=XYXY;
(B) each of W, X and Y is a base in which either:
  (i) (a) W=one of A, T/U, G, and C,
    X=one of A, T/U, G, and C,
    Y=one of A, T/U, G, and C,
    and each of W, X and Y is selected so as to be different from all of the others of W, X and Y,
    (b) an unselected said base of (i) (a) can be substituted any number of times for any one of W, X and Y, or
  (ii) (a) W=G or C,
    X=A or T/U,
    Y=A or T/U,
    and X≠Y, and
    (b) a base not selected in (ii)(a) can be inserted into each sequence at one or more locations, the location of each insertion being the same in all the sequences;
(C) up to three bases can be inserted at any location of any of the sequences or up to three bases can be deleted from any of the sequences;
(D) all of the sequences of a said group of oligonucleotides are read 5' to 3' or are read 3' to 5'; and wherein each oligonucleotide of a said set has a sequence of at least ten contiguous bases of the sequence on which it is based, provided that:
(E) the quotient of the sum of G and C divided by the sum of A, T/U, G and C for all combined sequences of the set is between about 0.1 and 0.40 and said quotient for each sequence of the set does not vary from the quotient for the combined sequences by more than 0.2; and
(F) for the group of 24mer sequences in which each 1=GATT, each 2=TGAT, each 3=AAAG, each 4=TGTA, each 5=GTAT, each 6=TTGA, each 7=TGAA, each 8=GTAA, each 9=ATTG, each 10=ATGA, each 11=TTAG, each 12=GTTA, each 13=ATAG, each 14=GTTT, each 15=GATG, each 16=GTAG, each 17=GAAG, each 18=GTTG, each 19=ATTA, each 20=TATA, each 21=TAAT and each 22=ATAT, for the group of sequences in which each 1=GATT, each 2=TGAT, each 3=AAAG, each 4=TGTA, each 5=GTAT, each 6=TTGA, each 7=TGAA, each 8=GTAA, each 9=ATTG, each 10=ATGA, each 11=TTAG, each 12=GTTA, each 13=ATAG, each 14=GTTT, each 15=GATG, each 16=GTAG, each 17=GAAG, each 18=GTTG, each 19=ATTA, each 20=TATA, each 21=TAAT and each 22=ATAT, under a defined set of conditions in which the maximum degree of hybridization between a sequence and any complement of a different sequence of the group of 24mer sequences does not exceed 30% of the degree of hybridization between said sequence and its complement, for all oligonucleotides of the set, the maximum degree of hybridization between an oligonucleotide and a complement of any other oligonucleotide of the set does not exceed 50% of the degree of hybridization of the oligonucleotide and its complement;

wherein any base present may be substituted by an analogue thereof.

Again, preferably, the contiguous bases of each oligonucleotide of a set are selected such that the position of the first base of each oligonucleotide within the sequence on which it is based is the same for all nucleotides of the set.

In a preferred aspect, subject to the provisos of (E) and (F) above, each oligonucleotide of a said set comprises a said sequence of twenty-four contiguous bases of the sequence on which it is based.

More preferably, subject to the proviso of (F) each oligonucleotide of a said set comprises a said sequence of twenty-four contiguous bases of the sequence on which it is based.

In particularly preferred aspects, in (B), W=one of G and C; X=one of A and T/U; and Y=one of A and T/U.

Even more preferred, in (B): W=G; X=one of A, and T/U; and Y=one of A and T/U.

In another broad aspect, the invention is a composition that includes fifty minimally cross-hybridizing molecules for use as tags or tag complements wherein each molecule comprises an oligonucleotide comprising a sequence of nucleotide bases for which, under a defined set of conditions, the maximum degree of hybridization between a said oligonucleotide and any complement of a different oligonucleotide does not exceed about 10% of the degree of hybridization between said oligonucleotide and its complement.

A preferred set of such defined conditions results in a level of hybridization that is the same as the level of hybridization obtained when hybridization conditions include 0.2 M NaCl, 0.1 M Tris, 0.08% Triton X-100, pH 8.0 at 37° C., and the sequences are covalently linked to microparticles. Of course, these conditions are preferably used directly.

Preferably, under the defined set of conditions, whatever the conditions are, the degree of hybridization between each oligonucleotide and its complement varies by a factor of between 1 and 8.

Preferably, each oligonucleotide is the same length and is at least twenty nucleotide bases in length. More preferably, each oligonucleotide is twenty-four nucleotide bases in length.

In certain embodiments, each molecule of a composition is linked to a solid phase support so as to be distinguishable from a mixture of said molecules by hybridization to its complement. Each such molecule can be linked to a defined location on such a solid phase support, the defined location for each molecule being different than the defined location for other, different, molecules.

In one preferred embodiment, the solid phase support is a microparticle and each said molecule is covalently attached to a different microparticle than each other different said molecule.

The invention includes kits for sorting and identifying polynucleotides. Such a kit can include one or more solid phase supports each having one or more spatially discrete regions, each such region having a uniform population of substantially identical tag complements covalently attached. The tag complements are made up of a set of oligonucleotides of the invention.

The one or more solid phase supports can be a planar substrate in which the one or more spatially discrete regions is a plurality of spatially addressable regions.

The tag complements can also be coupled to microparticles. Microparticles preferably each have a diameter in the range of from 5 to 40 µm.

Such a kit preferably includes microparticles that are spectrophotometrically unique, and therefore distinguishable from each other according to conventional laboratory techniques. Of course for such kits to work, each type of microparticle would generally have only one tag complement associated with it, and usually there would be a different oligonucleotide tag complement associated with (attached to) each type of microparticle.

The invention includes methods of using families of oligonucleotides of the invention.

One such method is of analyzing a biological sample containing a biological sequence for the presence of a mutation or polymorphism at a locus of the nucleic acid. The method includes:

(A) amplifying the nucleic acid molecule in the presence of a first primer having a 5'-sequence having the sequence of a tag complementary to the sequence of a tag complement belonging to a family of tag complements of the invention to form an amplified molecule with a 5'-end with a sequence complementary to the sequence of the tag;

(B) extending the amplified molecule in the presence of a polymerase and a second primer having 5'-end complementary the 3'-end of the amplified sequence, with the 3'-end of the second primer extending to immediately adjacent said locus, in the presence of a plurality of nucleoside triphosphate derivatives each of which is: (i) capable of incorporation during transcription by the polymerase onto the 3'-end of a growing nucleotide strand; (ii) causes termination of polymerization; and (iii) capable of differential detection, one from the other, wherein there is a said derivative complementary to each possible nucleotide present at said locus of the amplified sequence;

(C) specifically hybridizing the second primer to a tag complement having the tag complement sequence of (A); and (D) detecting the nucleotide derivative incorporated into the second primer in (B) so as to identify the base located at the locus of the nucleic acid.

In another method of the invention, a biological sample containing a plurality of nucleic acid molecules is analyzed for the presence of a mutation or polymorphism at a locus of each nucleic acid molecule, for each nucleic acid molecule. This method includes steps of:

(A) amplifying the nucleic acid molecule in the presence of a first primer having a 5'-sequence having the sequence of a tag complementary to the sequence of a tag complement belonging to a family of tag complements of the invention to form an amplified molecule with a 5'-end with a sequence complementary to the sequence of the tag;

(B) extending the amplified molecule in the presence of a polymerase and a second primer having 5'-end complementary the 3'-end of the amplified sequence, the 3'-end of the second primer extending to immediately adjacent said locus, in the presence of a plurality of nucleoside triphosphate derivatives each of which is: (i) capable of incorporation during transcription by the polymerase onto the 3'-end of a growing nucleotide strand; (ii) causes termination of polymerization; and (iii) capable of differential detection, one from the other, wherein there is a said derivative complementary to each possible nucleotide present at said locus of the amplified molecule;

(C) specifically hybridizing the second primer to a tag complement having the tag complement sequence of (A); and (D) detecting the nucleotide derivative incorporated into the second primer in (B) so as to identify the base located at the locus of the nucleic acid;

wherein each tag of (A) is unique for each nucleic acid molecule and steps (A) and (B) are carried out with said nucleic molecules in the presence of each other.

Another method includes analyzing a biological sample that contains a plurality of double stranded complementary nucleic acid molecules for the presence of a mutation or polymorphism at a locus of each nucleic acid molecule, for each nucleic acid molecule. The method includes steps of:

(A) amplifying the double stranded molecule in the presence of a pair of first primers, each primer having an identical 5'-sequence having the sequence of a tag complementary to the sequence of a tag complement belonging to a family of tag complements of the invention to form amplified molecules with 5'-ends with a sequence complementary to the sequence of the tag;

(B) extending the amplified molecules in the presence of a polymerase and a pair of second primers each second primer having a 5'-end complementary a 3'-end of the amplified sequence, the 3'-end of each said second primer extending to immediately adjacent said locus, in the presence of a plurality of nucleoside triphosphate derivatives each of which is: (i) capable of incorporation during transcription by the polymerase onto the 3'-end of a growing nucleotide strand; (ii) causes termination of polymerization; and (iii) capable of differential detection, one from the other;

(C) specifically hybridizing each of the second primers to a tag complement having the tag complement sequence of (A); and (D) detecting the nucleotide derivative incorporated into the second primers in (B) so as to identify the base located at said locus;

wherein the sequence of each tag of (A) is unique for each nucleic acid molecule and steps (A) and (B) are carried out with said nucleic molecules in the presence of each other.

In yet another aspect, the invention is a method of analyzing a biological sample containing a plurality of nucleic acid molecules for the presence of a mutation or polymorphism at a locus of each nucleic acid molecule, for each nucleic acid molecule, the method including steps of:

(a) hybridizing the molecule and a primer, the primer having a 5'-sequence having the sequence of a tag complementary to the sequence of a tag complement belonging to a family of tag complements of the invention and a 3'-end extending to immediately adjacent the locus;

(b) enzymatically extending the 3'-end of the primer in the presence of a plurality of nucleoside triphosphate derivatives each of which is: (i) capable of enzymatic incorporation onto the 3'-end of a growing nucleotide strand; (ii) causes termination of said extension; and (iii) capable of differential detection, one from the other, wherein there is a said derivative complementary to each possible nucleotide present at said locus;

(c) specifically hybridizing the extended primer formed in step (b) to a tag complement having the tag complement sequence of (a); and (d) detecting the nucleotide derivative incorporated into the primer in step (b) so as to identify the base located at the locus of the nucleic acid molecule;

wherein each tag of (a) is unique for each nucleic acid molecule and steps (a) and (b) are carried out with said nucleic molecules in the presence of each other.

The derivative can be a dideoxy nucleoside triphosphate.

Each respective complement can be attached as a uniform population of substantially identical complements in spacially discrete regions on one or more solid phase support(s).

Each tag complement can include a label, each such label being different for respective complements, and step (d) can include detecting the presence of the different labels for respective hybridization complexes of bound tags and tag complements.

Another aspect of the invention includes a method of determining the presence of a target suspected of being contained in a mixture. The method includes the steps of:

(i) labelling the target with a first label;
(ii) providing a first detection moiety capable of specific binding to the target and including a first tag;
(iii) exposing a sample of the mixture to the detection moiety under conditions suitable to permit (or cause) said specific binding of the molecule and target;
(iv) providing a family of suitable tag complements of the invention wherein the family contains a first tag complement having a sequence complementary to that of the first tag;
(v) exposing the sample to the family of tag complements under conditions suitable to permit (or cause) specific hybridization of the first tag and its tag complement;
(vi) determining whether a said first detection moiety hybridized to a first said tag complement is bound to a said labelled target in order to determine the presence or absence of said target in the mixture.

Preferably, the first tag complement is linked to a solid support at a specific location of the support and step (vi) includes detecting the presence of the first label at said specified location.

Also, the first tag complement can include a second label and step (vi) includes detecting the presence of the first and second labels in a hybridized complex of the moiety and the first tag complement.

Further, the target can be selected from the group consisting of organic molecules, antigens, proteins, polypeptides, antibodies and nucleic acids. The target can be an antigen and the first molecule can be an antibody specific for that antigen.

The antigen is usually a polypeptide or protein and the labelling step can include conjugation of fluorescent molecules, digoxigenin, biotinylation and the like.

The target can be a nucleic acid and the labelling step can include incorporation of fluorescent molecules, radiolabelled nucleotide, digoxigenin, biotinylation and the like.

DETAILED DESCRIPTION OF THE INVENTION

FIGURES

Reference is made to the attached figures in which,

FIGS. 1A and 1B illustrate results obtained in the cross-hybridization experiments described in Example 1. FIG. 1A shows the hybridization pattern found when a microarray containing all 100 probes (SEQ ID NOs:1 to 100) was hybridized with a 24mer oligonucleotide having the complementary sequence to SEQ ID NO:3 (target). FIG. 1B shows the pattern observed when a similar array was hybridized with a mix of all 100 targets, i.e., oligonucleotides having the sequences complementary to SEQ ID NOs:1 to 100.

DETAILED EMBODIMENTS

Figure 1B:
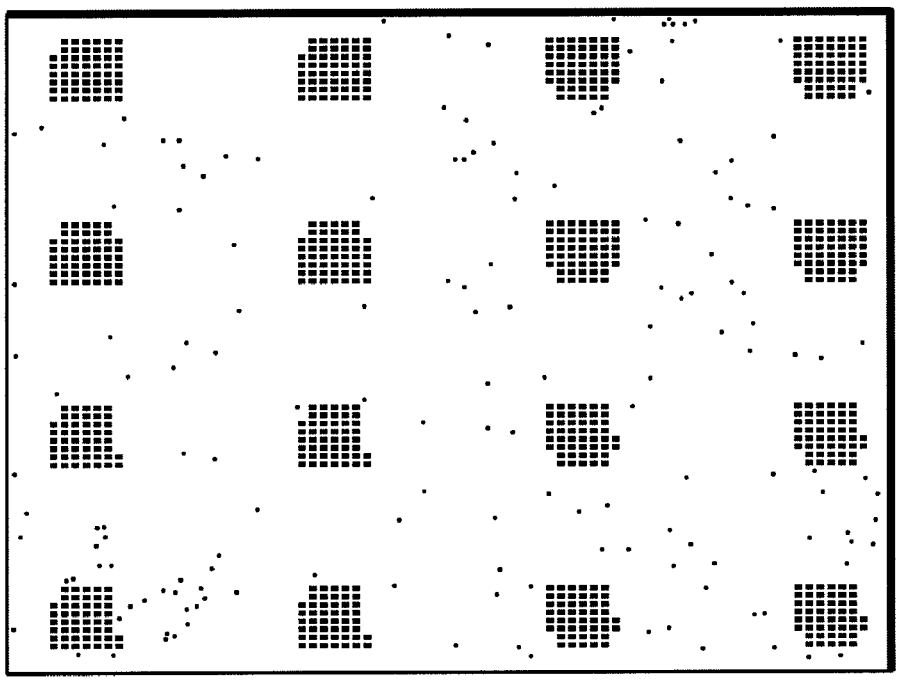

The invention provides a family of minimally cross-hybridizing sequences. The invention includes a method for sorting complex mixtures of molecules by the use of families of the sequences as oligonucleotide sequence tags. The families of oligonucleotide sequence tags are designed so as to provide minimal cross hybridization during the sorting process. Thus any sequence within a family of sequences will not cross hybridize with any other sequence derived from that family under appropriate hybridization conditions known by those skilled in the art. The invention is particularly useful in highly parallel processing of analytes.

Families of Oligonucleotide Sequence Tags

The present invention includes a family of 24mer polynucleotides, that have been demonstrated to be minimally cross-hybridizing with each other. This family of polynucleotides is thus useful as a family of tags, and their complements as tag complements.

The oligonucleotide sequences that belong to families of sequences that do not exhibit cross hybridization behavior can be derived by computer programs (described in international patent publication NO. WO 01/59151). The programs use a method of generating a maximum number of minimally cross-hybridizing polynucleotide sequences that can be summarized as follows. First, a set of sequences of a given length are created based on a given number of block elements. Thus, if a family of polynucleotide sequences 24 nucleotides (24mer) in length is desired from a set of 6 block elements, each element comprising 4 nucleotides, then a family of 24mers is generated considering all positions of the 6 block elements. In this case, there will be $6^6$ (46,656) ways of assembling the 6 block elements to generate all possible polynucleotide sequences 24 nucleotides in length.

Constraints are imposed on the sequences and are expressed as a set of rules on the identities of the blocks such that homology between any two sequences will not exceed the degree of homology desired between these two sequences. All polynucleotide sequences generated which obey the rules are saved. Sequence comparisons are performed in order to generate an incidence matrix. The incidence matrix is presented as a simple graph and the sequences with the desired property of being minimally cross hybridizing are found from a clique of the simple graph, which may have multiple cliques. Once a clique containing a suitably large number of sequences is found, the sequences are experimentally tested to determine if it is a set of minimally cross hybridizing sequences. This method has been used to obtain the 100 non cross-hybridizing tags of Table I that are the subject of this patent application.

The method includes a rational approach to the selection of groups of sequences that are used to describe the blocks. For example there are $n^4$ different tetramers that can be obtained from n different nucleotides, non-standard bases or analogues thereof. In a more preferred embodiment there are $4^4$ or 256 possible tetramers when natural nucleotides are used. More preferably 81 possible tetramers when only 3 bases are used A, T and G. Most preferably 32 different tetramers when all sequences have only one G.

Block sequences can be composed of a subset of natural bases most preferably A, T and G. Sequences derived from blocks that are deficient in one base possess useful characteristics, for example, in reducing potential secondary structure formation or reduced potential for cross hybridization with nucleic acids in nature. Sets of block sequences that are most preferable in constructing families of non cross hybridizing tag sequences should contribute approximately equivalent stability to the formation of the correct duplex as all other block sequences of the set. This should provide tag sequences that behave isothermally. This can be achieved for example by maintaining a constant base composition for all block sequences such as one G and three A's or T's for each block sequence. Preferably, non-cross hybridizing sets of block sequences will be comprised from blocks of sequences that are isothermal. The block sequences should be different from each other by at least one mismatch. Guidance for selecting such sequences is provided by methods for selecting primer and or probe sequences that can be found in published techniques (Robertson et al., Methods Mol Biol; 98:121-54 (1998); Rychlik et al, Nucleic Acids Research, 17:8543-8551 (1989); Breslauer et al., Proc Natl Acad Sci., 83:3746-3750 (1986)) and the like. Additional sets of sequences can be designed by extrapolating on the original family of non cross hybridizing sequences by simple methods known to those skilled in the art.

Figure 1A:
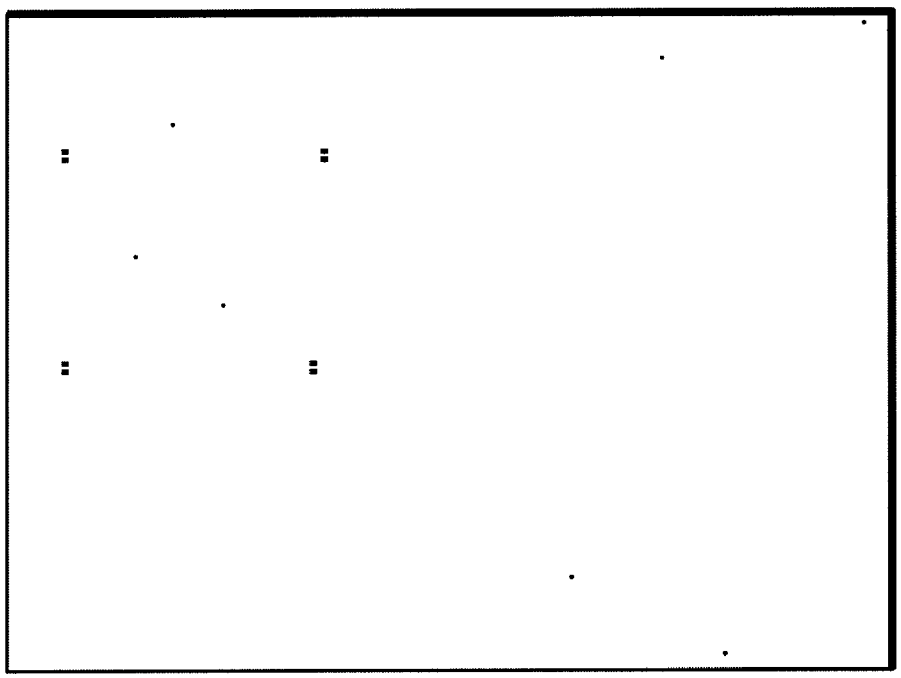

A preferred family of 100 tags is shown as SEQ ID NOs:1 to 100 in Table I. Characterization of the family of 100 sequence tags was performed to determine the ability of these sequences to form specific duplex structures with their complementary sequences and to assess the potential for cross hybridization. The 100 sequences were synthesized and spotted onto glass slides where they were coupled to the surface by amine linkage. Complementary tag sequences were Cy3-labeled and hybridized individually to the array containing the family of 100 sequence tags. Formation of duplex structures was detected and quantified for each of the positions on the array. Each of the tag sequences performed as expected, that is the perfect match duplex was formed in the absence of significant cross hybridization under stringent hybridization conditions. The results of a sample hybridization are shown in FIG. 1. FIG. 1a shows the hybridization pattern seen when a microarray containing all 100 probes was hybridized with the target complementary to probe 181234. The 4 sets of paired spots correspond to the probe complementary to the target. FIG. 1b shows the pattern seen when a similar array was hybridized with a mix of all 100 targets. These results indicate that the family of sequences which is the subject of this patent can be used as a family of non-cross hybridizing (tag) sequences.

The family of 100 non-cross-hybridizing sequences can be expanded by incorporating additional tetramer sequences that are used in constructing further 24mer oligonucleotides. In one example, four additional words were included in the generation of new sequences to be considered for inclusion as non-cross talkers in a family of sequences that were obtained from the above method using 10 tetramers. In this case, the four additional words were selected to avoid potential homologies with all potential combinations of other words: YYXW (TTAG); WYYX (GTTA); XYXW (ATAG) and WYYY (GTTT). The total number of sequences containing six words using the 14 possible words is $14^6$ or 7,529,536. These sequences were screened to eliminate sequences that contain repetitive regions that present potential hybridization problems such as four or more of a similar base (e.g., AAAA or TTTT) or pairs of G's. Each of these sequences was compared to the sequence set of the original family of 100 non-cross-hybridizing sequences (SEQ ID NOs:1 to 100). Any new sequence that contained a minimal threshold of homology (that does not include the use of insertions or deletions) such as 15 or more matches with any of the original family of sequences was eliminated. In other words, if it was possible to align a new sequence with one or more of the original 100 sequences so as to obtain a maximum simple homology of $15/24$ or more, the new sequence was dropped. "Simple homology" between a pair of sequences is defined here as the number of pairs of nucleotides that are matching (are the same as each other) in a comparison of two aligned sequences divided by the total number of potential matches. "Maximum simple homology" is obtained when two sequences are aligned with each other so as to have the maximum number of paired matching nucleotides. In any event, the set of new sequences so obtained was referred to as the "candidate sequences". One of the candidate sequences was arbitrarily chosen and referred to as sequence 101. All the candidate sequences were checked against sequence 101, and sequences that contained 15 or more non-consecutive matches (i.e., a maximum simple homology of $15/24$ (62.5%) or more were eliminated. This results in a smaller set of candidate sequences from which another sequence is selected that is now referred to as sequence 102. The smaller set of candidate sequences is now compared to sequence 102 eliminating sequences that contained 15 or more non-consecutive matches and the process is repeated until there are no candidate sequences remaining. Also, any sequence selected from the candidate sequences is eliminated if it has 13 or more consecutive matches with any other previously selected candidate sequence.

The additional set of 73 tag sequences so obtained (SEQ ID NOs:101 to 173) is composed of sequences that when compared to any of SEQ ID NOs:1 to 100 of Table I have no greater similarity than the sequences of the original 100 sequence tags of Table I. The sequence set as derived from the original family of non cross hybridizing sequences, SEQ ID NOs:1 to 173, are expected to behave with similar hybridization properties to the sequences having SEQ ID NOs:1 to 100 since it is understood that sequence similarity correlates directly with cross hybridization (Southern et al., Nat. Genet.; 21, 5-9: 1999).

The set of 173 24mer oligonucleotides were expanded to include those having SEQ ID NOs:174 to 210 as follows. The 4mers WXYW, XYXW, WXXW, WYYW, XYYX, YXYX, YXXY and XYXY where W=G, X=A, and Y=U/T were used in combination with the fourteen 4mers used in the generation of SEQ ID NOs:1 to 173 to generate potential 24-base oligonucleotides. Excluded from the set were those containing the sequence patterns GG, AAAA and TTTT. To be included in the set of additional 24mers, a sequence also had to have at least one of the 4mers containing two G's: WXYW (GATG), WYXW (GTAG), WXXW (GAAG), WYYW (GTTG) while also containing exactly six G's. Also required for a 24mer to be included was that there be at most six bases between every neighboring pair of G's. Another way of putting this is that there are at most six non-G's between any two G's. Also, each G nearest the 5'-end of its oligonucleotide (the left-hand side as written in Table I) was required to occupy one of the first to seventh positions (counting the 5'-terminal position as the first position.) A set of candidate sequences was obtained by eliminating any new sequence that was found to have a maximum simple homology of $16/24$ or more with any of the previous set of 173 oligonucleotides (SEQ ID NOs:1 to 173). As above, an arbitrary $174^{th}$ sequence was chosen and candidate sequences eliminated by comparison therewith. In this case the permitted maximum degree of simple homology was $16/24$. A second sequence was also eliminated if there were ten consecutive matches between the two (i.e., it was notionally possible to generate a phantom sequence containing a sequence of 10 bases that is identical to a sequence in each of the sequences being compared). A second sequence was also eliminated if it was possible to generate a phantom sequence 20 bases in length or greater.

A property of the polynucleotide sequences shown in Table I is that the maximum block homology between any two sequences is never greater than 66⅔ percent. This is because the computer algorithm by which the sequences were initially generated was designed to prevent such an occurrence. It is within the capability of a person skilled in the art, given the family of sequences of Table I, to modify the sequences, or add other sequences while largely retaining the property of minimal-cross hybridization which the polynucleotides of Table I have been demonstrated to have.

There are 210 polynucleotide sequences given in Table I. Since all 210 of this family of polynucleotides can work with each other as a minimally cross-hybridizing set, then any plurality of polynucleotides that is a subset of the 210 can also act as a minimally cross-hybridizing set of polynucleotides. An application in which, for example, 30 molecules are to be sorted using a family of polynucleotide tags and tag complements could thus use any group of 30 sequences shown in Table I. This is not to say that some subsets may be found in practical sense to be more preferred than others. For example, it may be found that a particular subset is more tolerant of a wider variety of conditions under which hybridization is conducted before the degree of cross-hybridization becomes unacceptable.

It may be desirable to use polynucleotides that are shorter in length than the 24 bases of those in Table I. A family of subsequences (i.e., subframes of the sequences illustrated) based on those contained in Table I having as few as 10 bases per sequence could be chosen, so long as the subsequences are chosen to retain homological properties between any two of the sequences of the family important to their non cross-hybridization.

The selection of sequences using this approach would be amenable to a computerized process. Thus for example, a string of the first 10 contiguous bases of the first 24mer of Table II could be selected:

GATTTGTATTGATTGAGATTAAAG. (SEQ ID NO: 1)

A string of the last 10 contiguous bases from the second 24mer could then be selected and compared for maximum homology against the first chosen sequence:

TGATTGTAGTATGTATTGATAAAG. (SEQ ID NO: 2)

Systematic pairwise comparison could then be carried out to determine if the maximum homology requirement of 66⅔ percent is violated:

| Alignment | | Matches |
|---|---|---|
|       GATTTGTATT | (SEQ ID NO: 216) | 1 |
| ATTGATAAAG | (SEQ ID NO: 217) | |
|      GATTTGTATT | (SEQ ID NO: 216) | 0 |
| ATTGATAAAG | (SEQ ID NO: 217) | |
|     GATTTGTATT | (SEQ ID NO: 216) | 1 |
| ATTGATAAAG | (SEQ ID NO: 217) | |
|    GATTTGTATT | (SEQ ID NO: 216) | 1 |
| ATTGATAAAG | (SEQ ID NO: 217) | |
|   GATTTGTATT | (SEQ ID NO: 216) | 1 |
| ATTGATAAAG | (SEQ ID NO: 217) | |
|  GATTTGTATT | (SEQ ID NO: 216) | 1 |

-continued

| Alignment | | Matches |
|---|---|---|
| ATTGATAAAG | (SEQ ID NO: 217) | |
| GATTTGTATT | (SEQ ID NO: 216) | 3 |
| ATTGATAAAG | (SEQ ID NO: 217) | |
| GATTTGTATT | (SEQ ID NO: 216) | 1 |
|  ATTGATAAAG | (SEQ ID NO: 217) | |
| GATTTGTATT | (SEQ ID NO: 216) | 2 |
|   ATTGATAAAG | (SEQ ID NO: 217) | |
| GATTTGTATT | (SEQ ID NO: 216) | 2 |
|    ATTGATAAAG | (SEQ ID NO: 217) | |
| GATTTGTATT | (SEQ ID NO: 216) | 5 (*) |
|     ATTGATAAAG | (SEQ ID NO: 217) | |
| GATTTGTATT | (SEQ ID NO: 216) | 3 |
|      ATTGATAAAG | (SEQ ID NO: 217) | |
| GATTTGTATT | (SEQ ID NO: 216) | 3 |
|       ATTGATAAAG | (SEQ ID NO: 217) | |
| GATTTGTATT | (SEQ ID NO: 216) | 2 |
|        ATTGATAAAG | (SEQ ID NO: 217) | |
| GATTTGTATT | (SEQ ID NO: 216) | 1 |
|         ATTGATAAAG | (SEQ ID NO: 217) | |
| GATTTGTATT | (SEQ ID NO: 216) | 1 |
|          ATTGATAAAG | (SEQ ID NO: 217) | |
| GATTTGTATT | (SEQ ID NO: 216) | 3 |
|           ATTGATAAAG | (SEQ ID NO: 217) | |
| GATTTGTATT | (SEQ ID NO: 216) | 1 |
|            ATTGATAAAG | (SEQ ID NO: 217) | |
| GATTTGTATT | (SEQ ID NO: 216) | 0 |
|             ATTGATAAAG | (SEQ ID NO: 217) | |

As can be seen, the maximum homology between the two selected subsequences is 50 percent (5 matches out of the total length of 10), and so these two sequences are compatible with each other.

A 10mer subsequence can be selected from the third 24mer sequence of Table I, and pairwise compared to each of the first two 1amer sequences to determine its computability therewith, etc. and in this way a family of 10mer sequences developed.

It is within the scope of this invention, to obtain families of sequences containing 11mer, 12mer, 13mer, 14mer, 15mer, 16mer, 17mer, 18mer, 19mer, 20mer, 21mer, 22mer and 23mer sequences by analogy to that shown for 10mer sequences.

It may be desirable to have a family of sequences in which there are sequences greater in length than the 24mer sequences shown in Table I. It is within the capability of a person skilled in the art, given the family of sequences shown in Table I, to obtain such a family of sequences. One possible approach would be to insert into each sequence at one or more locations a nucleotide, non natural base or analogue such that the longer sequence should not have greater similarity than any two of the original non cross hybridizing sequences of Table I and the addition of extra bases to the tag sequences should not result in a major change in the thermodynamic properties of the tag sequences of that set for example the GC content must be maintained between 10%-40% with a variance from the average of 20%. This method of inserting bases could be used to obtain a family of sequences up to 40 bases long.

Given a particular family of sequences that can be used as a family of tags (or tag complements), e.g., those of Table I or Table II, or the combined sequences of these two tables, a skilled person will readily recognize variant families that work equally as well.

Again taking the sequences of Table I for example, every T could be converted to an A and vice versa and no significant change in the cross-hybridization properties would be expected to be observed. This would also be true if every G were converted to a C.

Also, all of the sequences of a family could be taken to be constructed in the 5'-3' direction, as is the convention, or all of the constructions of sequences could be in the opposite direction (3'-5').

There are additional modifications that can be carried out. For example, C has not been used in the family of sequences. Substitution of C in place of one or more G's of a particular sequence would yield a sequence that is at least as low in homology with every other sequence of the family as the particular sequence chosen to be modified was. It is thus possible to substitute C in place of one or more G's in any of the sequences shown in Table I. Analogously, substituting of C in place of one or more A's is possible, or substituting C in place of one or more T's is possible.

It is preferred that the sequences of a given family are of the same, or roughly the same length. Preferably, all the sequences of a family of sequences of this invention have a length that is within five bases of the base-length of the average of the family. More preferably, all sequences are within four bases of the average base-length. Even more preferably, all or almost all sequences are within three bases of the average base-length of the family. Better still, all or almost all sequences have a length that is within one of the base-length of the average of the family.

It is also possible for a person skilled in the art to derive sets of sequences from the family of sequences that is the subject of this patent and remove sequences that would be expected to have undesirable hybridization properties.

Methods for Synthesis of Oligonucleotide Families

Preferably oligonucleotide sequences of the invention are synthesized directly by standard phosphoramidite synthesis approaches and the like (Caruthers et al, Methods in Enzymology; 154, 287-313: 1987; Lipshutz et al, Nature Genet.; 21, 20-24: 199; Fodor et al, Science; 251, 763-773: 1991). Alternative chemistries involving non natural bases such as peptide nucleic acids or modified nucleosides that offer advantages in duplex stability may also be used (Hacia et al; Nucleic Acids Res; 27: 4034-4039, 1999; Nguyen at al, Nucleic Acids Res.; 27, 1492-1498: 1999; Weiler et al, Nucleic Acids Res.; 25, 2792-2799: 1997). It is also possible to synthesize the oligonucleotide sequences of this invention with alternate nucleotide backbones such as phosphorothioate or phosphoroamidate nucleotides. Methods involving synthesis through the addition of blocks of sequence in a stepwise manner may also be employed (Lyttle at al, Biotechniques, 19: 274-280 (1995). Synthesis may be carried out directly on the substrate to be used as a solid phase support for the application or the oligonucleotide can be cleaved from the support for use in solution or coupling to a second support.

Solid Phase Supports

There are several different solid phase supports that can be used with the invention. They include but are not limited to slides, plates, chips, membranes, beads, microparticles and the like. The solid phase supports can also vary in the materials that they are composed of including plastic, glass, silicon, nylon, polystyrene, silica gel, latex and the like. The surface of the support is coated with the complementary sequence of the same.

In preferred embodiments, the family of tag complement sequences are derivatized to allow binding to a solid support. Many methods of derivatizing a nucleic acid for binding to a solid support are known in the art (Hermanson G., Bioconjugate Techniques; Acad. Press: 1996). The sequence tag may be bound to a solid support through covalent or non-covalent bonds (Iannone et al, Cytometry; 39: 131-140, 2000; Matson et al, Anal. Biochem.; 224: 110-106, 1995; Proudnikov et al, Anal Biochem; 259: 34-41, 1998; Zanimatteo et al, Analytical Biochemistry; 280:143-150, 2000). The sequence tag can be conveniently derivatized for binding to a solid support by incorporating modified nucleic acids in the terminal 5' or 3' locations.

A variety of moieties useful for binding to a solid support (e.g., biotin, antibodies, and the like), and methods for attaching them to nucleic acids, are known in the art. For example, an amine-modified nucleic acid base (available from, eg., Glen Research) may be attached to a solid support (for example, Covalink-NH, a polystyrene surface grafted with secondary amino groups, available from Nunc) through a bifunctional crosslinker (e.g., bis(sulfosuccinimidyl suberate), available from Pierce). Additional spacing moieties can be added to reduce steric hindrance between the capture moiety and the surface of the solid support.

Attaching Tags to Analytes for Sorting

A family of oligonucleotide tag sequences can be conjugated to a population of analytes most preferably polynucleotide sequences in several different ways including but not limited to direct chemical synthesis, chemical coupling, ligation, amplification, and the like. Sequence tags that have been synthesized with primer sequences can be used for enzymatic extension of the primer on the target for example in PCR amplification.

Detection of Single Nucleotide Polymorphisms Using Primer Extension

There are a number of areas of genetic analysis where families of non cross hybridizing sequences can be applied including disease diagnosis, single nucleotide polymorphism analysis, genotyping, expression analysis and the like. One such approach for genetic analysis referred to as the primer extension method (also known as Genetic Bit Analysis (Nikiforov et al, Nucleic Acids Res.; 22, 4167-4175: 1994; Head et al Nucleic Acids Res.; 25, 5065-5071: 1997)) is an extremely accurate method for identification of the nucleotide located at a specific polymorphic site within genomic DNA. In standard primer extension reactions, a portion of genomic DNA containing a defined polymorphic site is amplified by PCR using primers that flank the polymorphic site. In order to identify which nucleotide is present at the polymorphic site, a third primer is synthesized such that the polymorphic position is located immediately 3' to the primer. A primer extension reaction is set up containing the amplified DNA, the primer for extension, up to 4 dideoxynucleoside triphosphates, each labelled with a different fluorescent dye and a DNA polymerase such as the Klenow subunit of DNA Polymerase 1. The use of dideoxy nucleotides ensure that a single base is added to the 3' end of the primer, a site corresponding to the polymorphic site. In this way the identity of the nucleotide present at a specific polymorphic site can be determined by the identity of the fluorescent dye-labelled nucleotide that is incorporated in each reaction. One major drawback to this approach is its low throughput. Each primer extension reaction is carried out independently in a separate tube.

Universal sequences can be used to enhance the throughput of primer extension assay as follows. A region of genomic DNA containing multiple polymorphic sites is amplified by PCR. Alternately, several genomic regions containing one or more polymorphic sites each are amplified together in a multiplexed PCR reaction. The primer extension reaction is carried out as described above except that the primers used are chimeric, each containing a unique universal tag at the 5' end and the sequence for extension at the 3' end. In this way, each gene-specific sequence would be associated with a specific universal sequence. The chimeric primers would be hybridized to the amplified DNA and primer extension carried out as described above. This would result in a mixed pool of extended primers, each with a specific fluorescent dye characteristic of the incorporated nucleotide. Following the primer extension reaction, the mixed extension reactions are hybridized to an array containing probes that are reverse complements of the universal sequences on the primers. This would segregate the products of a number of primer extension reactions into discrete spots. The fluorescent dye present at each spot would then identify the nucleotide incorporated at each specific location.

Kits Using Families of Tag Sequences

The families of non cross-hybridizing sequences may be provided in kits for use in for example genetic analysis. Such kits include at least one set of non cross hybridizing sequences in solution or on a solid support. Preferably the sequences are attached to microparticles and are provided with buffers and reagents that are appropriate for the application. Reagents may include enzymes, nucleotides, fluorescent labels and the like that would be required for specific applications. Instructions for correct use of the kit for a given application will be provided.

EXAMPLES

Example 1

Demonstration of Non Cross Talk Behavior on Solid Array

One hundred oligonucleotide probes corresponding to a family of non-cross talking oligonucleotides from Table I were synthesized by Integrated DNA Technologies (IDT, Coralville Iowa). These oligonucleotides incorporated a $C_6$ aminolink group coupled to the 5' end of the oligo through a $C_{18}$ ethylene glycol spacer. These probes were used to prepare microarrays as follows. The probes were resuspended at a concentration of 50 µM in 150 mM NaPO4, pH 8.5. The probes were spotted onto the surface of a SuperAldehyde slide (Telechem Int., Sunnyvale Calif.) using an SDDC-II microarray spotter (ESI, Toronto Ontario, Canada). The spots formed were approximately 120 µM in diameter with 200 µM centre-to-centre spacing. Each probe was spotted 8 times on each microarray. Following spotting, the arrays were processed essentially as described by the slide manufacturer. Briefly, the arrays were treated with 67 mM sodium borohydride in PBS/EtOH (3:1) for 5 minutes then washed with 4 changes of 0.1% SDS. The arrays were not boiled.

One hundred labelled oligonucleotide targets were also synthesized by IDT. The sequence of these targets corresponded to the reverse complement of the 100 probe sequences. The targets were labelled at the 5' end with Cy3.

Each Cy3-labeled target oligonucleotide was hybridized separately to two microarrays each of which contained all 100 oligonucleotide probes. Hybridizations were carried out at 42° C. for 2 hours in a 40 µl reaction and contained 40 nM of the labelled target suspended in 10 mM TrisHCl, pH 8.3, 50 mM KCl, 0.1% Tween 20. These are low stringency hybridization conditions designed to provide a rigorous test of the performance of the family of non-cross hybridizing sequences. Hybridizations were carried out by depositing the hybridization solution on a clean cover slip then carefully positioning the microarray slide over the cover slip in order to avoid bubbles. The slide was then inverted and transferred to a humid chamber for incubation. Following hybridization, the cover slip was removed and the microarray was washed in hybridization buffer for 15 minutes at room temperature. The slide was then dried by brief centrifugation.

Hybridized microarrays were scanned using a ScanArray Lite (GSI-Lumonics, Billerica Mass.). The laser power and photomultiplier tube voltage used for scanning each hybridized microarray were optimized in order to maximize the signal intensity from the spots representing the perfect match.

The results of a sample hybridization are shown in FIGS. 1A and 1B. FIG. 1A shows the hybridization pattern seen when a microarray containing all 100 probes was hybridized with the target complementary to probe 181234. The 4 sets of paired spots correspond to the probe complementary to the target. FIG. 1b shows the pattern seen when a similar array was hybridized with a mix of all 100 targets.

Similar results to those illustrated in FIG. 1a were obtained for all of the sequences tested, and the feasibility of the use of molecules containing oligonucleotides containing SEQ ID NOs:1 to 100 as a set of tags (or tag complements) is thus established.

Example 2

Cross Talk Behavior of Sequence on Beads

A group of 100 of the sequences of Table I was tested for feasibility for use as a family of minimally cross-hybridizing oligonucleotides. The 100 sequences selected are separately indicated in Table I along with the numbers assigned to the sequences in the tests.

The tests were conducted using the Luminex LabMAP™ platform available from Luminex Corporation, Austin, Tex., U.S.A. The one hundred sequences, used as probes, were synthesized as oligonucleotides by Integrated DNA Technologies (IDT, Coralville, Iowa, U.S.A.). Each probe included a $C_6$ aminolink group coupled to the 5'-end of the oligonucleotide through a $C_{12}$ ethylene glycol spacer. The $C_6$ aminolink molecule is a six carbon spacer containing an amine group that can be used for attaching the oligonucleotide to a solid support. One hundred oligonucleotide targets (probe complements), the sequence of each being the reverse complement of the 100 probe sequences, were also synthesized by IDT. Each target was labelled at its 5'-end with biotin. All oligonucleotides were purified using standard desalting procedures, and were reconstituted to a concentration of approximately 200 μM in sterile, distilled water for use. Oligonucleotide concentrations were determined spectrophotometrically using extinction coefficients provided by the supplier.

Each probe was coupled by its amino linking group to a carboxylated fluorescent microsphere of the LabMAP system according to the Luminex[100] protocol. The microsphere, or bead, for each probe sequence has unique, or spectrally distinct, light absorption characteristics which permits each probe to be distinguished from the other probes. Stock bead pellets were dispersed by sonication and then vortexing. For each bead population, approximately five million microspheres (400 μL) were removed from the stock tube using barrier tips and added to a 1.5 mL Eppendorf tube (USA Scientific). The microspheres were then centrifuged, the supernatant was removed, and beads were resuspended in 25 μL of 0.2 M MES (2-(N-morpholino)ethane sulfonic acid) (Sigma), pH 4.5, followed by vortexing and sonication. One nmol of each probe (in a 25 μL volume) was added to its corresponding bead population. A volume of 2.5 μL of EDC cross-linker (1-ethyl-3-(3-dimethylaminopropyl)carbodiimide hydrochloride (Pierce), prepared immediately before use by adding 1.0 mL of sterile $ddH_2O$ to 10 mg of EDC powder, was added to each microsphere population. Bead mixes were then incubated for 30 minutes at room temperature in the dark with periodic vortexing. A second 2.5 μL aliquot of freshly prepared EDC solution was then added followed by an additional 30 minute incubation in the dark. Following the second EDC incubation, 1.0 mL of 0.02% Tween-20 (BioShop) was added to each bead mix and vortexed. The microspheres were centrifuged, the supernatant was removed, and the beads were resuspended in 1.0 mL of 0.1% sodium dodecyl sulfate (Sigma). The beads were centrifuged again and the supernatant removed. The coupled beads were resuspended in 100 μL of 0.1 M MES pH 4.5. Bead concentrations were then determined by diluting each preparation 100-fold in $ddH_2O$ and enumerating using a Neubauer BrightLine Hemacytometer. Coupled beads were stored as individual populations at 2-8° C. protected from light.

The relative oligonucleotide probe density on each bead population was assessed by Terminal Deoxynucleotidyl Transferase (TdT) end-labelling with biotin-ddUTPs. TdT was used to label the 3'-ends of single-stranded DNA with a labeled ddNTP. Briefly, 180 μL of the pool of 100 bead populations (equivalent to about 4000 of each bead type) to be used for hybridizations was pipetted into an Eppendorf tube and centrifuged. The supernatant was removed, and the beads were washed in 1×TdT buffer. The beads were then incubated with a labelling reaction mixture, which consisted of 5×TdT buffer, 25 mM $CoCl_2$, and 1000 pmol of biotin-16-ddUTP (all reagents were purchased from Roche). The total reaction volume was brought up to 85.5 μL with sterile, distilled $H_2O$, and the samples were incubated in the dark for 1 hour at 37° C. A second aliquot of enzyme was added, followed by a second 1 hour incubation. Samples were run in duplicate, as was the negative control, which contained all components except the TdT. In order to remove unincorporated biotin-ddUTP, the beads were washed 3 times with 200 μL of hybridization buffer, and the beads were resuspended in 50 μL of hybridization buffer following the final wash. The biotin label was detected spectrophotometrically using SA-PE (streptavidin-phycoerythrin conjugate). The streptavidin binds to biotin and the phycoerythrin is spectrally distinct from the probe beads. The 10 mg/mL stock of SA-PE was diluted 100-fold in hybridization buffer, and 15 μL of the diluted SA-PE was added directly to each reaction and incubated for 15 minutes at 37° Celsius. The reactions were analyzed on the Luminex[100] LabMAP. Acquisition parameters were set to measure 100 events per bead using a sample volume of 50 μL.

Figure 2:
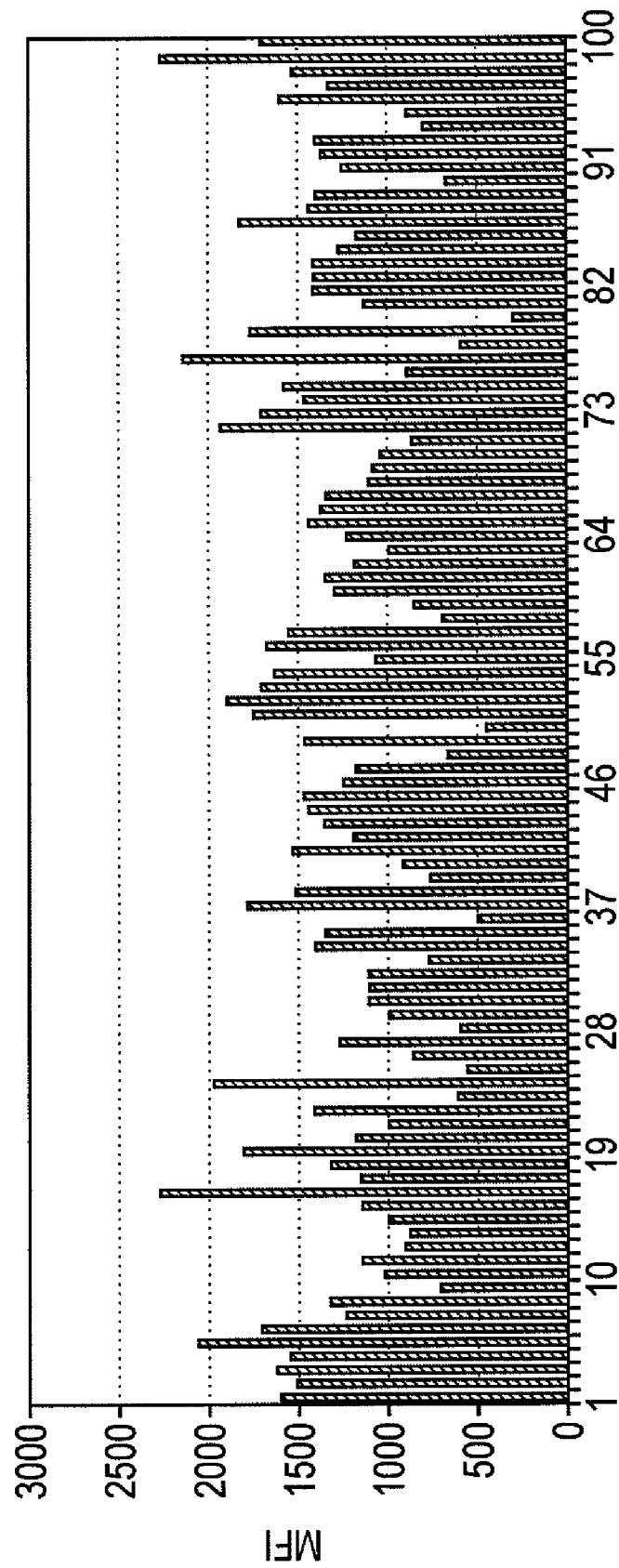
FIG. 2 shows the intensity of the signal (MFI) for each perfectly matched sequence (indicated in Table I) and its complement obtained as described in Example 2.

The results obtained are shown in FIG. 2. As can be seen the Mean Fluorescent Intensity (MFI) of the beads varies from 277.75 to 2291.08, a range of 8.25-fold. Assuming that the labelling reactions are complete for all of the oligonucleotides, this illustrates the signal intensity that would be obtained for each type of bead at this concentration if the target (i.e., labelled complement) was bound to the probe sequence to the full extent possible.

The cross-hybridization of targets to probes was evaluated as follows. 100 oligonucleotide probes linked to 100 different bead populations, as described above, were combined to generate a master bead mix, enabling multiplexed reactions to be carried out. The pool of microsphere-immobilized probes was then hybridized individually with each biotinylated target. Thus, each target was examined individually for its specific hybridization with its complementary bead-immobilized sequence, as well as for its non-specific hybridization with the other 99 bead-immobilized universal sequences present in the reaction. For each hybridization reaction, 25 μL bead mix (containing about 2500 of each bead population in hybridization buffer) was added to each well of a 96-well Thermowell PCR plate and equilibrated at 37° C. Each target was diluted to a final concentration of 0.002 fmol/μL in hybridization buffer; and 25 μL (50 fmol) was added to each well, giving a final reaction volume of 50 μL. Hybridization buffer consisted of 0.2 M NaCl, 0.1 M Tris, 0.08% Triton X-100, pH 8.0 and hybridizations were performed at 37° C. for 30 minutes. Each target was analyzed in triplicate and six background samples (i.e. no target) were, included in each plate. A SA-PE conjugate was used as a reporter, as described above. The 10 mg/mL stock of SA-PE was diluted 100-fold in hybridization buffer, and 15 μL of the diluted SA-PE was added directly to each reaction, without removal of unbound target, and incubated for 15 minutes at 37° C. Finally, an additional 35 μL of hybridization buffer was added to each well, resulting in a final volume of 100 μL per well prior to analysis on the Luminex[100] LabMAP. Acquisition parameters were set to measure 100 events per bead using a sample volume of 80 μL.

The percent hybridization was calculated for any event in which the NET MFI was at least 3 times the zero target background. In other words, a calculation was made for any sample where $(MFI_{sample} - MFI_{zero\ target\ background}) / MFI_{zero\ target\ background} \geq 3$.

A "positive" cross-talk event (i.e., significant mismatch or cross-hybridization) was defined as any event in which the net median fluorescent intensity $(MFI_{sample} - MFI_{zero\ target\ background})$ generated by a mismatched hybrid was greater than or equal to the arbitrarily set limit of 10% that of the perfectly matched hybrid determined under identical conditions. As there are 100 probes and 100 targets, there are 100×100=10,0000 possible different interactions possible of which 100 are the result of perfect hybridizations. The remaining 9900 result from hybridization of a target with a mismatched probe.

Figure 3:
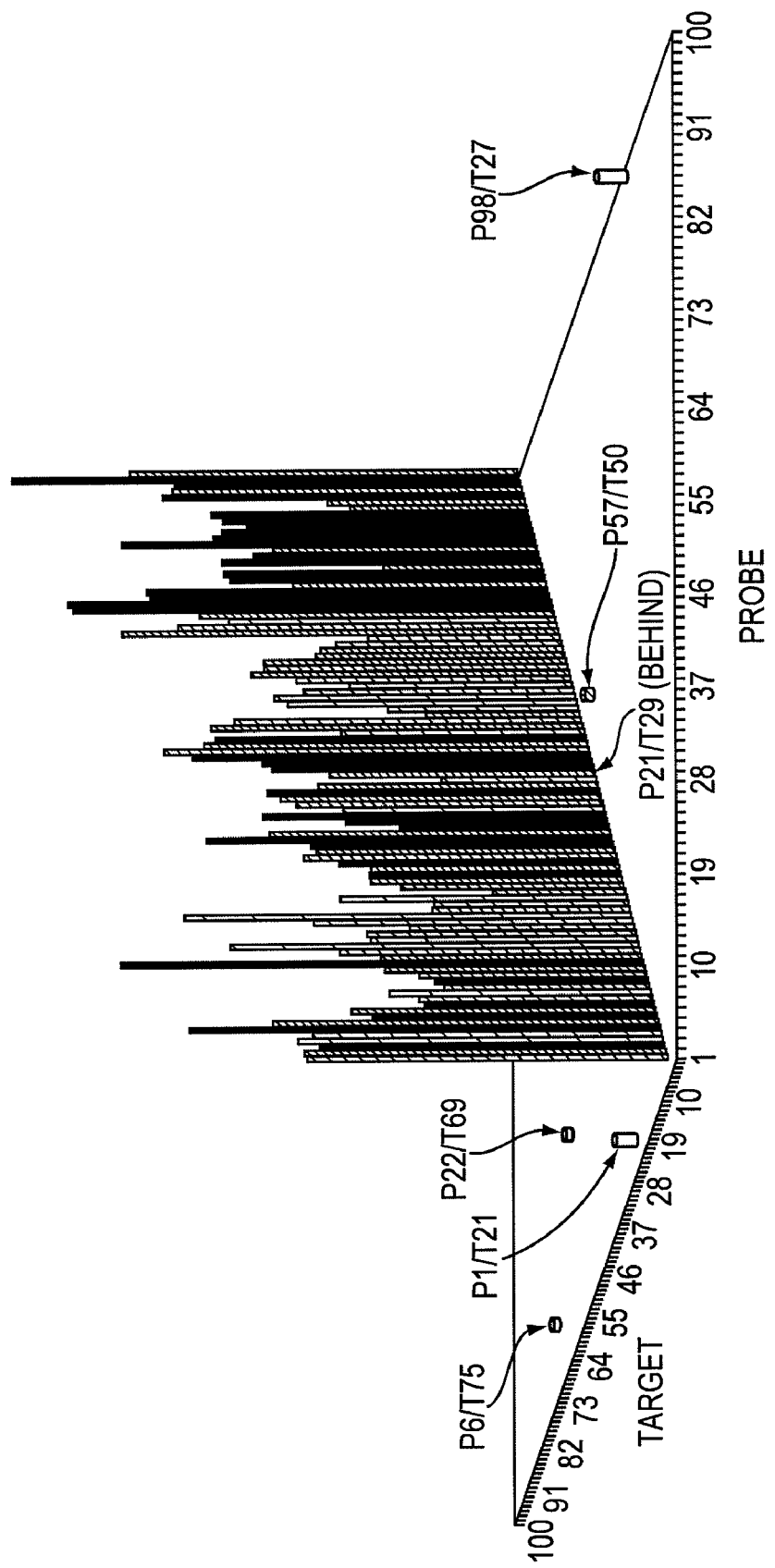
FIG. 3 is a three dimensional representation showing cross-hybridization observed for the sequences of FIG. 2 as described in Example 2. The results shown in FIG. 2 are reproduced along the diagonal of the drawing.

The results obtained are illustrated in FIG. 3. The ability of each target to be specifically recognized by its matching probe is shown. Of the possible 9900 non-specific hybridization events that could have occurred when the 100 targets were each exposed to the pool of 100 probes, 6 events were observed. Of these 6 events, the highest non-specific event generated a signal equivalent to 10.2% of the signal observed for the perfectly matched pair (i.e. specific hybridization event).

Figure 4:
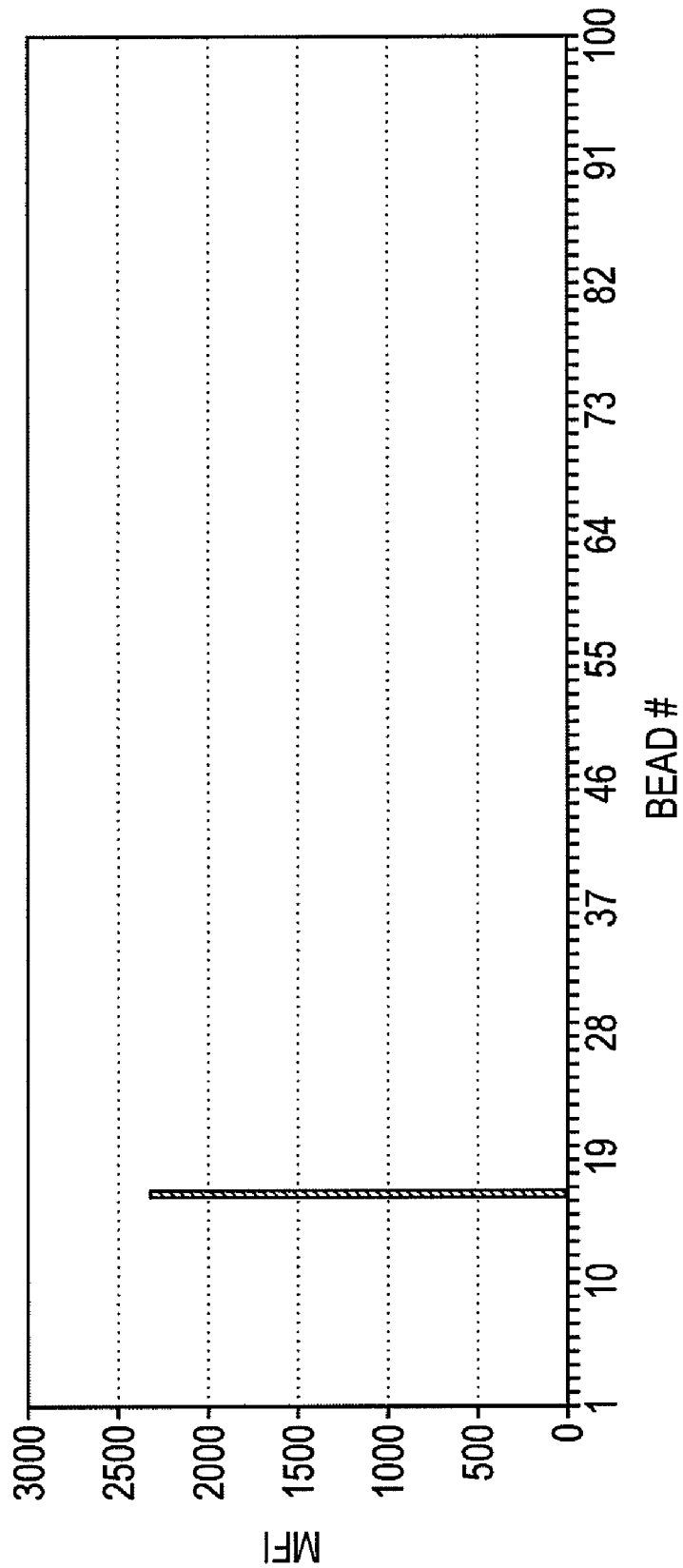
FIG. 4 is illustrative of results obtained for an individual target (SEQ ID NO:23, target No. 16) when exposed to the 100 probes of Example 2. The MFI for each bead is plotted.

Each of the 100 targets was thus examined individually for specific hybridization with its complement sequence as incorporated onto a microsphere, as well as for non-specific hybridization with the complements of the other 99 target sequences. Representative hybridization results for target 16 (complement of probe 16, Table I) are shown in FIG. 4. Probe 16 was found to hybridize only to its perfectly-matched target. No cross-hybridization with any of the other 99 targets was observed.

The foregoing results demonstrate the possibility of incorporating the 210 sequences of Table I, or any subset thereof, into a multiplexed system with the expectation that most if not all sequences can be distinguished from the others by hybridization. That is, it is possible to distinguish each target from the other targets by hybridization of the target with its precise complement and minimal hybridization with complements of the other targets.

Example 3

Tag Sequences Used in Sorting Polynucleotides

The family of non cross hybridizing sequence tags or a subset thereof can be attached to oligonucleotide probe sequences during synthesis and used to generate amplified probe sequences. In order to test the feasibility of PCR amplification with non cross hybridizing sequence tags and subsequently addressing each respective sequence to its appropriate location on two-dimensional or bead arrays, the following experiment was devised. A 24mer tag sequence was connected in a 5'-3' specific manner to a p53 exon specific sequence (20mer reverse primer). The connecting p53 sequence represented, the inverse complement of the nucleotide gene sequence. To facilitate the subsequent generation of single stranded DNA post-amplification the tag-Reverse primer was synthesized with a phosphate modification ($PO_4$) on the 5'-end. A second PCR primer was also generated for each desired exon, which represented the Forward (5'-3') amplification primer. In this instance the Forward primer was labeled with a 5'-biotin modification to allow detection with Cy3-avidin or equivalent.

A practical example of the aforementioned description is as follows:

For exon 1 of the human p53 tumor suppressor gene sequence the following tag-Reverse primer was generated (SEQ ID NO: 213):

```
                    222087                        222063
5'-PO4- GATTGTAAGATTTGATAAAGTGTA-TCCAGGGAAGCGTGTCACCGTCGT-3'
         Tag Sequence #3                   Exon 1 Reverse
```

The numbering above the Exon-1 reverse primer represents the genomic nucleotide positions of the indicated bases.

The corresponding Exon-1 Forward primer sequence is as follows:

```
                                      (SEQ ID NO: 214)
              221873              221896
   5'-Biotin-TCATGGCGACTGTCCAGCTTTGTG-3'
```

In combination these primers will amplify a product of 214 by plus a 24 by tag extension yielding a total size of 238 bp. Once amplified, the PCR product was purified using a QIAquick PCR purification kit and the resulting DNA was quantified.

To generate single stranded DNA, the DNA was subjected to X-exonuclease digestion thereby resulting in the exposure of a single stranded sequence (anti-tag) complementary to the tag-sequence covalently attached to the solid phase array. The resulting product was heated to 95° C. for 5 minutes and then directly applied to the array at a concentration of 10-50 nM. Following hybridization and concurrent sorting, the tag-Exon 1 sequences were visualized using Cy3-streptavidin. In addition to direct visualization of the biotinylated product, the product itself can now act as a substrate for further analysis of the amplified region, such as SNP detection and haplotype determination.

A number of additional methods for the detection of single nucleotide polymorphisms, including but not limited to, allele specific polymerase chain reaction (ASPCR), allele specific primer extension (ASPE) and oligonucleotide ligation assay (OLA) can be performed by those skilled in the art in combination with the tag sequences described herein.

DEFINITIONS

Non cross hybridizations Describes the absence of hybridization between two sequences that are not perfect complements of each other.

Cross Hybridization: The hydrogen bonding of a single-stranded DNA sequence that is partially but not entirely complementary to a single-stranded substrate.

Homology: How closely related two or more separate strands of DNA are to each other, based on their base sequences.

Analogue: A chemical which resembles a nucleotide base. A base which does not normally appear in DNA but can substitute for the ones which do, despite minor differences in structure.

Complement: The opposite or "mirror" image of a DNA sequence. A complementary DNA sequence has an "A" for every "T" and a "C" for every "G". Two complementary strands of single stranded DNA, for example a tag sequence and it's complement, will join to form a double-stranded molecule.

Complementary DNA (cDNA): DNA that is synthesized from a messenger RNA template; the single-stranded form is often used as a probe in physical mapping.

Oligonucleotide: Refers to a short nucleotide polymer whereby the nucleotides may be natural nucleotide bases or analogues thereof.

Tag: Refers to an oligonucleotide that can be used for specifically sorting analytes with at least one other oligonucleotide that when used together do not cross hybridize.

Similar Homology: In the context of this invention, pairs of sequences are compared with each other based on the amount of "homology" between the sequences. By way of example, two sequences are said to have a 50% "maximum homology" with each other if, when the two sequences are aligned side-by-side with each other so to obtain the (absolute) maximum number of identically paired bases, the number of identically paired bases is 50% of the total number of bases in one of the sequences. (If the sequences being compared are of different lengths, then it would be of the total number of bases in the shorter of the two sequences.) Examples of determining maximum homology are as follows:

Example 4

Determining Maximum Homology

```
      *   *
A-A-B-B-C-C
    B-D-C-D-D-D  (2 out of 4 paired bases are the same)

*   *
A-A-B-B-C-C
      B-D-C-D-D-D  (2 out of 3 paired bases are the same)
```

In this case, the maximum number of identically paired bases is two and there are two possible alignments yielding this maximum number. The total number of possible pairings is six giving 33⅓% (⅔) homology. The maximum amount of homology between the two sequences is thus ⅓.

Example 5

Determining Maximum Homology

```
* *     *
A-A-B-B-C-A
A-A-D-D-C-D  (3 out of 6 paired bases are the same)
```

In this alignment, the number of identically paired bases is three and the total number of possibly paired bases is six, so the homology between the two sequences is 3/6 (50%).

```
        *
A-A-B-B-C-A
        A-A-D-D-C-D  (1 out of 1 paired bases are the same)
```

In this alignment, the number of identically paired bases is 1, so the homology between the two sequences is 1/6 (16⅔%).

The maximum homology between these two sequences is thus 50%.

Block sequence: Refers to a symbolic representation of a sequence of blocks. In its most general form a block sequence is a representative sequence in which no particular value, mathematical variable, or other designation is assigned to each block of the sequence.

Incidence Matrix: As used herein is a well-defined term in the field of Discrete Mathematics. However, an incidence matrix cannot be defined without first defining a "graph". In the method described herein a subset of general graphs called simple graphs is used. Members of this subcategory are further defined as follows.

A simple graph G is a pair (V, E) where V represents the set of vertices of the simple graph and E is a set of un-oriented edges of the simple graph. An edge is defined as a 2-component combination of members of the set of vertices. In other words, in a simple graph G there are some pairs of vertices that are connected by an edge. In our application a graph is based on nucleic acid sequences generated using sequence templates and vertices represent DNA sequences and edges represent a relative property of any pair of sequences.

The incidence matrix is a mathematical object that allows one to describe any given graph. For the subset of simple graphs used herein, the simple graph $G=(V,E)$, and for a pre-selected and fixed ordering of vertices, $V=\{v_1, v_2, \ldots, v_n\}$, elements of the incidence matrix $A(G)=[a_{ij}]$ are defined by the following rules:

(1) $a_{ij}=1$ for any pair of vertices $\{v_i,v_j\}$ that is a member of the set of edges; and (2) $a_{ij}=0$ for any pair of vertices $\{v_i,v_j\}$ that is not a member of the set of edges.

This is an exact unequivocal definition of the incidence matrix. In effect, one selects the indices: 1, 2, ... n of the vertices and then forms an (n×n) square matrix with elements $a_{ij}=1$ if the vertices $v_i$ and $v_j$ are connected by an edge and $a_{ij}=0$ if the vertices $v_i$ and $v_j$ are not connected by an edge.

To define the term "class property" as used herein, the term "complete simple graph" or "clique" must first be defined. The complete simple graph is required because all sequences that result from the method described herein should collectively share the relative property of any pair of sequences defining an edge of graph G, for example not violating the threshold rule that is, do not have a "maximum simple homology" greater than a predetermined amount, whatever pair of the sequences are chosen from the final set. It is possible that additional "local" rules, based on known or empirically determined behavior of particular nucleotides, or nucleotide sequences, are applied to sequence pairs in addition to the basic threshold rule.

In the language of a simple graph, $G=(V, E)$, this means in the final graph there should be no pair of vertices (no sequence pair) not connected by an edge (because an edge means that the sequences represented by $v_i$ and $v_j$ do not violate the threshold rule).

Because the incidence matrix of any simple graph can be generated by the above definition of its elements, the consequence of defining a simple complete graph is that the corresponding incidence matrix for a simple complete graph will have all off-diagonal elements equal to 1 and all diagonal elements equal to 0. This is because if one aligns a sequence with itself, the threshold rule is of course violated, and all other sequences are connected by an edge.

For any simple graph, there might be a complete subgraph. First, the definition of a subgraph of a graph is as follows. The subgraph $Gs=(Vs,Es)$ of a simple graph $G=(V,E)$ is a simple graph that contains the subsets of vertices Vs of the set V of vertices and inclusion of the set Vs into the set V is immersion (a mathematical term). This means that one generates a subgraph $Gs=(Vs,Es)$ of a simple graph G in two steps. First select some vertices Vs from G. Then select those edges Es from G that connect the chosen vertices and do not select edges that connect selected with non selected vertices.

We desire a subgraph of G that is a complete simple graph. By using this property of the complete simple graph generated from the simple graph G of all sequences generated by the template based algorithm, the pairwise property of any pair of the sequences (violating/non-violating the threshold rule) is converted into the property of all members of the set, termed "the class property".

By selecting a subgraph of a simple graph G that is a complete simple graph, this assures that, up to the tests involving the local rules described herein, there are no pairs of sequences in the resulting set that violate the threshold rule, also described above, independent of which pair of sequences in the set are chosen. This feature is called the "desired class property".

The present invention thus includes reducing the potential for non cross-hybridization behavior by taking into account local homologies of the sequences and appears to have greater rigor than known approaches. For example, the method described herein involves the sliding of one sequence relative to the other sequence in order to form a sequence alignment that would accommodate insertions or deletions. (Kane et al., Nucleic Acids Res.; 28, 4552-4557: 2000).

TABLE I

| SEQ ID NO(1) | Sequence | No Assigned in Example 2(2) |
|---|---|---|
| 1 | GATTTGTATTGATTGAGATTAAAG | 1 |
| 2 | TGATTGTAGTATGTATTGATAAAG | 2 |
| 3 | GATTGTAAGATTTGATAAAGTGTA | 3 |
| 4 | GATTTGAAGATTATTGGTAATGTA | 4 |
| 5 | GATTGATTATTGTGATTTGAATTG | 5 |
| 6 | GATTTGATTGTAAAAGATTGTTGA | 6 |
| 7 | ATTGGTAAATTGGTAAATGAATTG | 7 |
| 8 | ATTGGATTTGATAAAGGTAAATGA | |
| 9 | GTAAGTAATGAATGTAAAAGGATT | 8 |
| 10 | GATTGATTGATTGATTGATTTGAT | |
| 11 | TGATGATTAAAGAAAGTGATTGAT | |
| 12 | AAAGGATTTGATTGATAAAGTGAT | |
| 13 | TGTAGATTTGTATGTATGTATGAT | 10 |
| 14 | GATTTGATAAAGAAAGGATTGATT | |
| 15 | GATTAAAGTGATTGATGATTTGTA | 11 |
| 16 | AAAGAAAGAAAGAAAGAAAGTGTA | 12 |
| 17 | TGTAAAAGGATTGATTTGTATGTA | |
| 18 | AAAGTGTAGATTGATTAAAGAAAG | |
| 19 | AAAGTTGATTGATTGAAAAGGTAT | |
| 20 | TTGATTGAGATTGATTTTGAGTAT | |
| 21 | TGAATTGATGAATGAATGAAGTAT | 15 |
| 22 | GTAATGAAGTATGTATGTAAGTAA | |
| 23 | TGATGATTTGAATGAAGATTGATT | 16 |
| 24 | TGATAAAGTGATAAAGGATTAAAG | 17 |

TABLE I-continued

| SEQ ID NO(1) | Sequence | No Assigned in Example 2(2) |
|---|---|---|
| 25 | TGATTTGAGTATTTGAGATTTTGA | 18 |
| 26 | TGTAGTAAGATTGATTAAAGGTAA | |
| 27 | GTATAAAGGATTGATTTTGAAAAG | |
| 28 | GTATTTGAGTAAGTAATTGATTGA | 19 |
| 29 | GTAAAAAGTTGAGTATTGAAAAAG | |
| 30 | GATTTGATAAAGGATTTGTATTGA | |
| 31 | GATTGTATTGAAGTATTGTAAAAG | 20 |
| 32 | TGATGATTTTGATGAAAAAGTTGA | |
| 33 | TGATTTGAGATTAAAGAAAGGATT | 21 |
| 34 | TGATTGAATTGAGTAAAAAGGATT | 22 |
| 35 | AAAGTGTAAAAGGATTTGATGTAT | |
| 36 | AAAGGTATTTGAGATTTGATTGAA | |
| 37 | AAAGTTGAGATTTGAATGATTGAA | 23 |
| 38 | TGTATTGAAAAGGTATGATTTGAA | |
| 39 | GTATTGTATTGAAAAGGTAATTGA | 24 |
| 40 | TTGAGTAATGATAAAGTGAAGATT | |
| 41 | TGAAGATTTGAAGTAATTGAAAAG | 25 |
| 42 | TGAAAAGTGTAGATTTTGAGTAA | 26 |
| 43 | TGTATGAATGAAGATTTGATTGTA | |
| 44 | AAAGTTGAGTATTGATTTGAAAAG | 27 |
| 45 | GATTTGTAGATTTGTATTGAGATT | |
| 46 | AAAGAAAGGATTTGTAGTAAGATT | 29 |
| 47 | GTAAAAAGAAAGGTATAAAGGTAA | 30 |
| 48 | GATTAAAGTTGATTGAAAAGTGAA | 31 |
| 49 | TGAAAAAGGTAATTGATGTATGAA | |
| 50 | AAAGGATTAAAGTGAAGTAATTGA | 33 |
| 51 | ATGAATTGGTATGTATATGAATGA | 34 |
| 52 | TGAAATGAATGAATGATGAAATTG | 35 |
| 53 | ATTGATTGTGAATGAAATGAATTG | 36 |
| 54 | ATTGAAAGATGAAAAGATGAAAAG | 37 |
| 55 | ATTGTTGAAAAGTGTAATGATTGA | 38 |
| 56 | ATGATGTAATGAAAAGATTGTGTA | 39 |
| 57 | AAAGATTGAAAGATGATGTAATTG | |
| 58 | ATTGATGAGTATATTGTGTAGTAA | 41 |
| 59 | AAAGATTGTGTAATTGATGATGAA | |
| 60 | AAAGGTATATTGTGTAATGAGTAA | |
| 61 | TGTAATGAGTATTGTAATTGAAAG | 43 |
| 62 | GTATAAAGAAAGATTGGTAAATGA | 44 |

TABLE I-continued

| SEQ ID NO(1) | Sequence | No Assigned in Example 2(2) |
|---|---|---|
| 63 | TTGAGTAATTGAATTGTGAAATGA | 45 |
| 64 | TGTATTGAATGAATTGTTGATGTA | 46 |
| 65 | TGTAATTGGTAAATGAGTAAAAAG | |
| 66 | TGAATGAAATTGATGAGTATAAAG | |
| 67 | GTAAGTAAATTGAAAGATTGATGA | 49 |
| 68 | GTAAATGATGATATTGGTATATTG | 50 |
| 69 | ATTGTTGATGATTGATTGAAATGA | 51 |
| 70 | ATTGTGAAGTATAAAGATGATTGA | 52 |
| 71 | ATGAAAAGTTGAGTAAATTGTGAT | |
| 72 | ATGAATTGAAAGTGATTGAAAAAG | 54 |
| 73 | GTAAATTGATGAAAAGTTGATGAT | |
| 74 | AAAGTGATGTATATGAGTAAAATTG | 56 |
| 75 | GTAATGATAAAGATGATGATATTG | 57 |
| 76 | TTGAAAAGATTGGTAATGATATGA | |
| 77 | AAAGTGAAAAGATTGATTGATGA | 59 |
| 78 | ATTGATGAGATTGATTATTGTGTA | |
| 79 | ATGAGATTATTGGATTTGTAGATT | 60 |
| 80 | TGAAGATTATGAATTGGTAAGATT | 61 |
| 81 | ATTGGATTATGAGATTATGATTGA | 62 |
| 82 | ATTGTTGAATTGGATTAAAGATGA | |
| 83 | AAAGATGAGTAAGTAAATTGGATT | |
| 84 | AAAGGTAAGATTATTGATGAAAAG | 65 |
| 85 | ATTGATGAGATTAAAGTTGAATTG | |
| 86 | GATTATTGGATTATGAAAAGGATT | |
| 87 | GATTTGTAATTGTTGAGTAAATGA | 67 |
| 88 | AAAGAAAGATTGTTGAGATTATGA | 68 |
| 89 | GTATAAAGGATTTTGAATTGATGA | |
| 90 | TTGAGATTGTAAATGAATTGTTGA | |
| 91 | GTATATTGATTGTGTAATGAAAAG | |
| 92 | TGATATGAATTGGATTATTGGTAT | 70 |
| 93 | ATGAATGATGAATGATGATTATTG | |
| 94 | ATGAATTGATTGGATTGTAATGAT | 71 |
| 95 | GATTGTAATTGAGTAAATTGATGA | |
| 96 | GATTATTGGATTAAAGGTAAATGA | 72 |
| 97 | ATTGTTGAATTGATGAGATTTGAT | 73 |
| 98 | GATTATGAGTAAATTGATTGTGAT | |
| 99 | GATTATTGTTGATGAATGATATTG | |
| 100 | TGTAAAAGATTGAAAGGTATGATT | 75 |
| 101 | GTATTTAGATGAGTTTGTTAGATT | 76 |
| 102 | TGAAGTTATGTAATAGAAAGTGAT | |
| 103 | GTATGTATTGTATGTAGTTAATTG | 77 |
| 104 | TGATATAGATAGTTAGATAGATAG | 78 |
| 105 | ATGATGATGTATTGTAGTTATGAA | 79 |
| 106 | TTAGTGAATGTATTAGTTGATGTA | |
| 107 | GTTAGTTAGATTATTGTTAGTTAG | 80 |
| 108 | GTTAATTGTGTAGTTTGTTATTGA | |
| 109 | GTTATGAAATAGTGATATTGTTAG | |
| 110 | ATTGTTAGAAAGTGTAGATTAAAG | 81 |
| 111 | ATGAGTATGTTATTAGTGTATGTA | 82 |
| 112 | TGTAATAGTGAAGTTAGATTGTAT | 83 |
| 113 | ATTGATAGATGATTAGTTAGTTGA | 84 |
| 114 | ATGAGTTTGTTTATGAGATTAAAG | |
| 115 | TGATGTTTGATTATGATGTAGTAT | 85 |
| 116 | ATGAGTTAGTTATGAATTAGATGA | |
| 117 | ATTGTTAGTGATGTTAGTAATTAG | 86 |
| 118 | TGATGTAAGTATTGATGTTAGTTT | 87 |
| 119 | GATTGTAAATAGAAAGTGAAGTAA | 88 |
| 120 | ATTGTGTATGAAGTATTGTATGAT | |
| 121 | ATAGTGATGTTATGAAGATTGTTA | |
| 122 | TTAGATGAATTGTGAAGTATTTAG | 90 |
| 123 | GTAAGTTATGATTGATGTTATGAA | 91 |
| 124 | GTATTGATGTTTAAAGTGTAATAG | 92 |
| 125 | GATTGTAAGTAAGATTGTATATTG | |
| 126 | GTTTGTATTTAGATGAATAGAAAG | 93 |
| 127 | GTTTGATTTGTAATAGTGATTGTA | |
| 128 | TGTATGTAGTATTTAGAAAGATGA | |
| 129 | ATGAATTGTGATAAAGAAAGTTAG | |
| 130 | TTAGTGTAGTAAGTTTAAAGTGTA | 95 |
| 131 | GTATGATTGTTTGTAATTAGTGAT | |
| 132 | GTTTAAAGTTAGTTGAGTTAGTAT | 96 |
| 133 | ATAGTGTATGTAGATTATGAGATT | 97 |
| 134 | TTGAATGATTAGTTGAGTATGATT | 98 |
| 135 | GTATGTAAGTTAGTATGATTTGAA | |
| 136 | TGTAGTATATTGTTGAATTGTGAT | |
| 137 | ATAGTGATTGTATGTATGATAAAG | |
| 138 | TTAGTGATTGATGTATATTGAAAG | |

TABLE I-continued

| SEQ ID NO(1) | Sequence | No Assigned in Example 2(2) |
|---|---|---|
| 139 | GTAAGATTATGAGTTATGATGTAA | |
| 140 | GTTATGAAATTGTTAGTGTAGATT | 99 |
| 141 | GTTAGATTTGTAGTTTAAAGATAG | 100 |
| 142 | TTAGTGATTGAAATGATGTAGATT | |
| 143 | AAAGTGTAGTTATTAGTTAGTTAG | |
| 144 | AAAGAAAGTGTATGATGTTATTAG | |
| 145 | GATTGTATATTGTGTATGATGATT | |
| 146 | TTGAGATTGTTATGATATGAGTAT | |
| 147 | ATGAGTATGATTGTTATGATGTTT | |
| 148 | TGATTTAGTGAAATTGTGTATTAG | |
| 149 | TGAATGTATGTAGTATGTTTGTTA | |
| 150 | GTTAGTATTGATGATTATGAGTTA | |
| 151 | GTATATTGTGATTTAGTTGAGATT | |
| 152 | GTTAGTTTAAAGTTGAGATTGTTT | |
| 153 | GTATATTGTTAGATGAGATTTGTA | |
| 154 | TGATGTATGTTAGTTTATGAATGA | |
| 155 | TGTAGTATGTAATGTAGTATTTGA | |
| 156 | ATGAGTTATGTATTGAGTTAGTAT | |
| 157 | TGTATGATGATTATAGTTGAGTAA | |
| 158 | ATTGATGAATGAGTTTGTATAAAG | |
| 159 | TTGAGTTTATGATTAGAAAGAAAG | |
| 160 | TGATATTGATGAGTTAGTATTGAA | |
| 161 | ATAGAAAGTGAAATGAGTATGTTA | |
| 162 | TTGATGTAGATTTGATGTATATAG | |
| 163 | TTGAGATTATAGTGTAGTTTATAG | |
| 164 | TGATGTTAGATTGTTTGATTATTG | |
| 165 | TGTATTAGATAGTGATTTGAATGA | |
| 166 | GATTATGATGAATGTAGTATGTAA | |
| 167 | TGAATGATTGATATGAATAGTGTA | |
| 168 | GTAATGATTTAGTGTATTGAGTTT | |
| 169 | TGTAGTAATGATTTGATGATAAAG | |
| 170 | TGAAGATTGTTATTAGTGATATTG | |
| 171 | GTATTTGAATGATGTAATAGTGTA | |
| 172 | GTATATGATGTATTAGATTGAAAG | |
| 173 | AAAGTTAGATTGAAAGTGATAAAG | |
| 174 | GTAAGATGTTGATATAGAAGATTA | 9 |
| 175 | TAATATGAGATGAAAGTGAATTAG | |
| 176 | TTAGTGAAGAAGTATAGTTTATTG | 13 |
| 177 | GTAGTTGAGAAGATAGTAATTAAT | |
| 178 | ATGAGATGATATTTGAGAAGTAAT | |
| 179 | GATGTGAAGAAGATGAATATATAT | |
| 180 | AAAGTATAGTAAGATGTATAGTAG | 14 |
| 181 | GAAGTAATATGAGTAGTTGAATAT | |
| 182 | TTGATAATGTTTGTTTGTTTGTAG | 28 |
| 183 | TGAAGAAGAAAGTATAATGATGAA | |
| 184 | GTAGATTAGTTTGAAGTGAATAAT | 32 |
| 185 | TATAGTAGTGAAGATGATATATGA | |
| 186 | TATAATGAGTTGTTAGATATGTTG | |
| 187 | GTTGTGAAATTAGATGTGAAATAT | |
| 188 | TAATGTTGTGAATAATGTAGAAAG | 40 |
| 189 | GTTTATAGTGAAATATGAAGATAG | 42 |
| 190 | ATTATGAAGTAAGTTAATGAGAAG | 47 |
| 191 | GATGAAAGTAATGTTTATTGTGAA | |
| 192 | ATTATTGAGATGTGAAGTTTGTTT | 48 |
| 193 | TGTAGAAGATGAGATGTATAATTA | 53 |
| 194 | TAATTTGAGTTGTGTATATAGTAG | |
| 195 | TGATATTAGTAAGAAGTTGAATAG | |
| 196 | GTTAGTTATTGAGAAGTGTATATA | 55 |
| 197 | GTAGTAATGTTAATGAATTAGTAG | 58 |
| 198 | GTTTGTTTGATGTGATTGAATAAT | |
| 199 | GTAAGTAGTAATTTGAATATGTAG | 64 |
| 200 | GTTTGAAGATATGTTTGAAGTATA | |
| 201 | ATGATAATTGAAGATGTAATGTTG | |
| 202 | GTAGATAGTATAGTTGTAATGTTA | 66 |
| 203 | GATGTGAATGTAATATGTTTATAG | 69 |
| 204 | TGAAATTAGTTTGTAAGATGTGTA | 74 |
| 205 | TGTAGTATAAAGTATATGAAGTAG | 63 |
| 206 | ATATGTTGTTGAGTTGATAGTATA | 89 |
| 207 | ATTATTGAGTAGAAAGATAGAAAG | 94 |
| 208 | GTTGTTGAATATTGAATATAGTTG | |
| 209 | ATGAGAAGTTAGTAATGTAAATAG | |
| 210 | TGAAATGAGAAGATTAATGAGTTT | |

(1) Oligonucleotides having SEQ ID NOs: 1 to 100 were used in experiments of Example 1.
(2) Oligonucleotides used in experiments of Example 2 are indicated in this column by the numbers assigned to them in the experiments.

All references referred to in this specification are incorporated herein by reference.

The scope of protection sought for the invention described herein is defined by the appended claims. It will also be understood that any elements recited above or in the claims, can be combined with the elements of any claim. In particular, elements of a dependent claim can be combined with any element of a claim from which it depends, or with any other compatible element of the invention.

The invention claimed is:

1. An oligonucleotide tag or tag complement for use in a multiplex assay, wherein the tag or tag complement is selected from the group of oligonucleotides consisting of:

| | |
|---|---|
| GTAAATGATGATATTGGTATATTG, | (SEQ ID NO: 68) |
| ATTGTTGATGATTGATTGAAATGA, | (SEQ ID NO: 69) |
| ATTGTGAAGTATAAAGATGATTGA, | (SEQ ID NO: 70) |
| ATGAATTGAAAGTGATTGAAAAAG, | (SEQ ID NO: 72) |
| AAAGTGATGTATATGAGTAAATTG, | (SEQ ID NO: 74) |
| GTAATGATAAAGATGATGATATTG, | (SEQ ID NO: 75) |
| AAAGTGAAAAAGATTGATTGATGA, | (SEQ ID NO: 77) |
| ATGAGATTATTGGATTTGTAGATT, | (SEQ ID NO: 79) |
| TGAAGATTATGAATTGGTAAGATT, and | (SEQ ID NO: 80) |
| ATTGGATTATGAGATTATGATTGA, | (SEQ ID NO: 81) | including oligonucleotides complementary thereto.

2. The oligonucleotide of claim 1, wherein one of the oligonucleotides in SEQ ID NOs: 68-70, 72, 74, 75, 77, and 79-81 does not cross-hybridize with a second, different oligonucleotide in SEQ ID NOs: 68-70, 72, 74, 75, 77, and 79-81 under the following hybridization conditions: 0.2 M NaCl, 0.1 M Tris, 0.08% Triton X-100, pH 8.0 at 37° C.

3. The oligonucleotide of claim 1, wherein the oligonucleotide is attached to a solid support.

4. The oligonucleotide of claim 3, wherein the solid support is a microparticle.

5. An improved method of analyzing a biological sample suspected of comprising a target, wherein the improvement comprises using the oligonucleotide tag or tag complement of claim 1.

6. A nucleic acid tag or tag complement comprising an oligonucleotide selected from the group of oligonucleotides consisting of: SEQ ID NO: 68, SEQ ID NO: 69, SEQ ID NO: 70, SEQ ID NO: 72, SEQ ID NO: 74, SEQ ID NO: 75, SEQ ID NO: 77, SEQ ID NO: 79, SEQ ID NO: 80, and SEQ ID NO: 81, or a sequence complementary thereto, wherein the oligonucleotide is attached to a solid support.

7. The nucleic acid of claim 6, wherein the solid support is a microparticle.

8. The nucleic acid of claim 6, wherein the oligonucleotide has the sequence set forth in SEQ ID NO: 68 or the sequence complementary thereto.

9. The nucleic acid of claim 6, wherein the oligonucleotide has the sequence set forth in SEQ ID NO: 69 or a sequence complementary thereto.

10. The nucleic acid of claim 6, wherein the oligonucleotide has the sequence set forth in SEQ ID NO: 70 or a sequence complementary thereto.

11. The nucleic acid of claim 6, wherein the oligonucleotide has the sequence set forth in SEQ ID NO: 72 or a sequence complementary thereto.

12. The nucleic acid of claim 6, wherein the oligonucleotide has the sequence set forth in SEQ ID NO: 74 or a sequence complementary thereto.

13. The nucleic acid of claim 6, wherein the oligonucleotide has the sequence set forth in SEQ ID NO: 75 or a sequence complementary thereto.

14. The nucleic acid of claim 6, wherein the oligonucleotide has the sequence set forth in SEQ ID NO: 77 or a sequence complementary thereto.

15. The nucleic acid of claim 6, wherein the oligonucleotide has the sequence set forth in SEQ ID NO: 79 or a sequence complementary thereto.

16. The nucleic acid of claim 6, wherein the oligonucleotide has the sequence set forth in SEQ ID NO: 80 or a sequence complementary thereto.

17. The nucleic acid of claim 6, wherein the oligonucleotide has the sequence set forth in SEQ ID NO: 81 or a sequence complementary thereto.

18. An improved method of analyzing a biological sample suspected of comprising a target, wherein the improvement comprises using the tag or tag complement of claim 6.

19. A kit for sorting and identifying polynucleotides, the kit comprising at least one oligonucleotide tag or tag complement of claim 6.

20. The kit of claim 19, wherein each different oligonucleotide is linked to a defined location on the solid support, the defined location for each said oligonucleotide being different and distinguishable from the defined location for each different oligonucleotide.

21. The kit of claim 20, wherein the solid support is a microparticle.

22. The kit of claim 21, wherein each different oligonucleotide is linked to a different microparticle, each microparticle being distinguishable from each other microparticle.

23. A combination of oligonucleotide tags or tag complements for use in a multiplexed assay comprising at least one oligonucleotide set forth in SEQ ID NOs: 68-70, 72, 74, 75, 77, or 79-81 and an oligonucleotide selected from the group consisting of SEQ ID NOs: 1-210, wherein the combination comprises at least two different oligonucleotides set forth in SEQ ID NOs: 1-210.

24. The combination of claim 23, wherein the oligonucleotides are linked to a solid support.

25. The combination of claim 24, wherein each different oligonucleotide is linked to a defined location on the solid support, the defined location for each said oligonucleotide being different than and distinguishable from the defined location for each different oligonucleotide.

26. The combination of claim 24, wherein the solid support is a microparticle.

27. The combination of claim 26, wherein each different oligonucleotide is linked to a different microparticle, each microparticle being distinguishable from each other microparticle.

28. A combination comprising a plurality of oligonucleotide tags or tag complements for use in a multiplexed assay, wherein the plurality of tags or tag complements comprise SEQ ID NOs: 68-70, 72, 74, 75, 77, and 79-81 and sequences complementary thereto.

* * * * *